(12) United States Patent
Fredriksson

(10) Patent No.: US 12,404,545 B1
(45) Date of Patent: *Sep. 2, 2025

(54) METHOD FOR MAKING A PHYSICAL MAP OF BINDING EVENTS THAT ARE ON OR ON CELLS

(71) Applicant: PIXELGEN TECHNOLOGIES AB, Stockholm (SE)

(72) Inventor: Simon Fredriksson, Bromma (SE)

(73) Assignee: PIXELGEN TECHNOLOGIES AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 19/212,481

(22) Filed: May 19, 2025

Related U.S. Application Data

(63) Continuation of application No. 19/049,977, filed on Feb. 10, 2025, which is a continuation of application
(Continued)

(51) Int. Cl.
C12Q 1/68 (2018.01)
C12Q 1/6844 (2018.01)
(Continued)

(52) U.S. Cl.
CPC ......... C12Q 1/6844 (2013.01); *C12Q 1/6804* (2013.01); *C12Q 1/6841* (2013.01);
(Continued)

(58) Field of Classification Search
None
See application file for complete search history.

(56) References Cited

U.S. PATENT DOCUMENTS

2005/0118616 A1* 6/2005 Kawashima ........... C12Q 1/682
435/6.12
2009/0233277 A1* 9/2009 Murakami ........... C12Q 1/6844
435/6.1
(Continued)

FOREIGN PATENT DOCUMENTS

JP 2007525174 A 9/2007
JP 2022513561 A 2/2022
(Continued)

OTHER PUBLICATIONS

Han, "Envisioning DNA as Photons, Broad Team Turns Sequencers Into Microscopes", GenomeWeb, Jun. 20, 2019.
(Continued)

*Primary Examiner* — Aaron A Priest
(74) *Attorney, Agent, or Firm* — James S. Keddie; Bozicevic, Field & Francis LLP

(57) ABSTRACT

Provided herein is a method comprising producing rolling circle amplification (RCA) products that are immobilized in or on cells, wherein each RCA product has an RCA product identifier sequence that distinguishes the RCA product from other RCA products that are immobilized in or on the cells; while the RCA products are immobilized in or on cells, producing nucleic acid products that contain RCA product identifier sequences or complements thereof from adjacent RCA products; for each of a plurality of the nucleic acid products, identifying which RCA product identifier sequences or complements thereof are in the nucleic acid product; and making a physical map of at least some of the RCA products using the identified RCA product identifier sequences or complements thereof.

13 Claims, 16 Drawing Sheets

Specification includes a Sequence Listing.

Related U.S. Application Data

No. 17/763,145, filed as application No. PCT/IB2020/060062 on Oct. 27, 2020, now Pat. No. 12,252,741.

(60) Provisional application No. 62/926,907, filed on Oct. 28, 2019.

(51) Int. Cl.
    *C12Q 1/6804*     (2018.01)
    *C12Q 1/6841*     (2018.01)

(52) U.S. Cl.
    CPC ............. *C12Q 2525/179* (2013.01); *C12Q 2531/125* (2013.01); *C12Q 2563/179* (2013.01); *C12Q 2565/50* (2013.01); *C12Q 2565/537* (2013.01); *C12Q 2600/16* (2013.01)

(56) References Cited

U.S. PATENT DOCUMENTS

| | | | |
|---|---|---|---|
| 2010/0240101 A1 | 9/2010 | Lieberman et al. | |
| 2015/0044674 A1 | 2/2015 | Fredriksson et al. | |
| 2015/0298091 A1 | 10/2015 | Weitz et al. | |
| 2016/0265046 A1 | 9/2016 | Zhang et al. | |
| 2016/0281134 A1 | 9/2016 | Wu | |
| 2016/0289750 A1* | 10/2016 | Landegren | C12Q 1/6876 |
| 2016/0376642 A1* | 12/2016 | Landegren | C12Q 1/6804 |
| | | | 435/6.11 |
| 2020/0063187 A1* | 2/2020 | Samusik | C12Q 1/6818 |
| 2021/0095331 A1 | 4/2021 | Fan et al. | |

FOREIGN PATENT DOCUMENTS

| | | |
|---|---|---|
| WO | WO 2012/057689 A1 | 5/2012 |
| WO | WO 2012/106385 A2 | 8/2012 |
| WO | WO 2012/112804 A1 | 8/2012 |
| WO | WO 2015/047186 A1 | 4/2015 |
| WO | WO 2015/058052 A1 | 4/2015 |
| WO | WO 2016/123419 A1 | 8/2016 |
| WO | WO 2017/044893 A1 | 3/2017 |
| WO | WO 2017/222453 A1 | 12/2017 |
| WO | WO 2019/099751 A1 | 5/2019 |
| WO | WO 2019/099751 A9 | 5/2019 |

OTHER PUBLICATIONS

Han, "SciLifeLab, Broad Institute Researchers Go High Definition With Spatial Transcriptomics", GenomeWeb, Sep. 12, 2019.

Hoffecker et al., "A computational framework for DNA sequencing microscopy", PNAS, Sep. 2019, 116(39): 19282-19287.

Stuart et al., "Integrative single-cell analysis", Nature Reviews Genetics, Jan. 2019, 20: 257-272.

Weinstein et al., "DNA Microscopy: Optics-free Spatio-genetic Imaging by a Stand-Alone Chemical Reaction", Cell, Jun. 2019, 178: 1-13.

Wu et al., "Profiling surface proteins on individual exosomes using a proximity barcoding assay", Nature Communications, Aug. 2019, 10: 3854, 10 pages.

Wu et al., "Profiling surface proteins on individual exosomes using a proximity barcoding assay" (Supplementary information), Nature Communications, Aug. 2019, 10: 3854, 12 pages.

Ke et al., "In situ sequencing for RNA analysis in preserved tissue and cells", Nature Methods, 2013, 10(9): 857-860.

Hoffecker et al., "A Computational Framework for DNA Sequencing-Based Microscopy", bioRxiv, Nov. 21, 2018.

Greenwood et al., "Proximity assays for sensitive quantification of proteins", Biomolecular Detection and Quantification, 2015, 4: 10-16.

\* cited by examiner

METHOD FOR MAKING A PHYSICAL MAP OF BINDING EVENTS THAT ARE ON OR ON CELLS

CROSS-REFERENCE TO RELATED APPLICATIONS

This application is a continuation of U.S. application Ser. No. 19/049,977, filed on Feb. 10, 2025, which is a continuation of U.S. application Ser. No. 17/763,145, filed on Mar. 23, 2022, which is a § 371 national phase of International Application No. PCT/IB2020/060062, filed on Oct. 27, 2020, which claims the benefit of U.S. provisional application Ser. No. 62/926,907, filed on Oct. 28, 2019, which applications are incorporated herein in their entireties.

INCORPORATION BY REFERENCE OF SEQUENCE LISTING PROVIDED AS A SEQUENCE LISTING XML FILE

A Sequence Listing is provided herewith as a Sequence Listing XML, "PIXL-001CON_SEQLIST.xml" created on Feb. 7, 2025 and having a size of 30,921 bytes. The contents of the Sequence Listing XML are incorporated by reference herein in their entirety.

BACKGROUND

Cell polarity, i.e., the skewing of markers to one or more areas within or on the surface of a cell, is a common phenomenon but it is difficult to study in a high throughput way. For example, while there are several methods for analyzing the expression of cell surface markers on single cells (e.g., methods that involve flow cytometry or placing individual cells into compartments and then performing an assay on the individual cells), those methods do not provide any information about the spatial relationships of cell surface markers on the individual cells. More recent methods for analyzing the spatial relationships between biological molecules in or on cells, e.g., proximity ligation assays (see, e.g., Söderberg et al Nature Methods. 2006 3:995-1000), Weinstein's diffusion-based method (see, e.g., Cell 2019 178:229-241 and US20160265046), and array-based methods (see, e.g., Vickovic et al, Nature Methods 2019 16:987-990) are either not readily adapted to the analysis of cell surface markers or they do not provide any information about cell polarity. Microscopy is the gold-standard for analyzing spatial relationships between markers on single cells. However, microscopy is inherently very low throughput and challenging to automate.

In view of the above, a need still exists for methods analyzing cell polarity in a high throughput manner.

SUMMARY

Described herein, among other things, is a sequencing-based method for analyzing the distribution of markers that may be in or on a cell. The method relies on immobilizing rolling circle amplification (RCA) products in or on a target (e.g., a cell or a substrate) mapping the RCA products relative to one another, and then mapping the location and quantity of markers onto the RCA products via a proximity assay.

In some embodiments, the method may comprise (a) producing a complex comprising population of grid oligonucleotide molecules and a population of RCA products that each have a unique RCA product identifier sequence, wherein the grid oligonucleotides are hybridized directly or indirectly via a splint to complementary sites in the RCA products; (b) extending the grid oligonucleotide molecules that are hybridized to two RCA products to add the complements of the unique RCA product identifier sequences from the two RCA products to the grid oligonucleotide molecules; (c) sequencing the extended grid oligonucleotides; (d) analyzing the sequences to identify which pairs of unique RCA product identifier sequence complements have been added onto the grid oligonucleotides; and (e) making one or more physical maps of the immobilized RCA products using the pairs of sequences identified in (d). This method is conceptually illustrated in FIG. 2, although several variations are possible.

The method may be practiced in a number of different ways. For example, as illustrated in FIGS. 13 and 14, the method may be implemented such that, in step (a), at least some of unique RCA product identifier sequences in the RCA products are double-stranded, and step step (b) comprises ligating the grid oligonucleotide molecules to the ends of the strands of the double-stranded regions of the RCA products, thereby adding the complements of the unique RCA product identifier sequences from the two RCA products to the grid oligonucleotides.

In other examples, as illustrated in FIGS. 6, 7, and 9-12, the method may be implemented such that, step (a) comprises hybridizing a population of grid oligonucleotide molecules with a population of RCA products, wherein either the grid oligonucleotide molecules or the RCA products are immobilized, wherein: (i) the RCA products of the population of RCA products each have a unique RCA product identifier sequence and a grid oligonucleotide binding sequence, and (ii) the grid oligonucleotide molecules each comprise a first terminal sequence that is complementary to a grid oligonucleotide binding sequence and a second terminal sequence that is complementary to a grid oligonucleotide binding sequence; and (iii) at least some of the grid oligonucleotide molecules hybridize to two adjacent RCA products. In these embodiments, the extending may comprise a gap fill and/or ligation reaction, which adds complements of the unique RCA product identifier sequences from the two adjacent RCA products to the grid oligonucleotide.

In some embodiments the grid oligonucleotide molecules may be made in situ (i.e., produced by ligation of two or more shorter oligonucleotides in a splint-mediated ligation reaction). Sec, e.g., FIG. 12. In other embodiments, intact grid oligonucleotide molecules are hybridized to sites in the sample. See, e.g., FIG. 10. In other embodiments, pre-made RCA products are hybridized to sites in the sample see, e.g., FIGS. 6 and 7. In other embodiments, the RCA products may be made in situ, in or on a cell. In situ production of RCA products has been described in a variety of publications. For example, Soderberg et al (Nat. Methods 2006 3:995-1000) describes an in situ proximity ligation assay (PLA) that generates RCA products in situ from co-incident binding of two antibodies that are attached to oligonucleotides, Leuchowius et al (Cytometry A. 2009 75:833-9) describes in situ PLA on cell surfaces for flow cytometry, Larsson et al. (Nat. Methods. 2010 7:395-7) describes detection of mRNA in cells by padlock probes and in situ RCA, Gusev et al (Am. J. Pathol. 2001 159:63-69) describes dingle protein detection in tissue and on surface of cells amplified by immuno-RCA, and Lizardi et al. (Nat Genet. 1998 19:225-32) describes a method for detecting point mutations in cells that uses in situ RCA.

In some embodiments, the method may comprise: (a) hybridizing a population of grid oligonucleotide molecules with a population of RCA products, wherein either the grid oligonucleotide molecules or the RCA products are immobilized in a cell or on one or more surfaces, e.g., a glass slide or cells, wherein: (i) the RCA products of the population of RCA products each have a unique RCA product identifier sequence and a grid oligonucleotide binding sequence, and (ii) the grid oligonucleotide molecules each comprise a first terminal sequence that is complementary to a grid oligonucleotide binding sequence and a second terminal sequence that is complementary to a grid oligonucleotide binding sequence; and (iii) at least some of the grid oligonucleotide molecules hybridize to two adjacent RCA products; (b) extending the grid oligonucleotide molecules that are hybridized to two adjacent RCA products to add the complements of the unique RCA product identifier sequences from two adjacent RCA products to the grid oligonucleotide, thereby producing extended grid oligonucleotides; (c) sequencing the extended grid oligonucleotides; and (d) analyzing the sequences to identify which pairs of unique RCA product identifier sequence complements have been added onto to the extended grid oligonucleotides.

In some embodiments, the method may comprise: (a) hybridizing a population of grid oligonucleotide molecules with a population of RCA products, wherein either the grid oligonucleotide molecules or the RCA product are immobilized in a cell or on one or more surfaces, e.g., a glass slide or cells, wherein: (i) the population of RCA products comprises: i. a first set of RCA products each comprising a repeated sequence comprising a unique RCA product identifier sequence and a first grid oligonucleotide binding sequence, and ii. a second set of RCA products comprising a repeated sequence comprising a unique RCA product identifier sequence and a second grid oligonucleotide binding sequence; (ii) the grid oligonucleotide molecules each comprise a first terminal sequence that is complementary to the first grid oligonucleotide binding sequence and a second terminal sequence that is complementary to the second grid oligonucleotide binding sequence; and (iii) at least some of the grid oligonucleotide molecules hybridize to two adjacent RCA products; (b) extending the grid oligonucleotide molecules that are hybridized to two adjacent RCA products to add the complements of the unique RCA product identifier sequences from two adjacent RCA products to the grid oligonucleotide, thereby producing extended grid oligonucleotides; (c) sequencing the extended grid oligonucleotides; and (d) analyzing the sequences to identify which pairs of unique RCA product identifier sequence complements have been added onto the grid oligonucleotides.

In any embodiment (and as illustrated in FIGS. 10-16) the grid oligonucleotide molecules may be immobilized in cells or on the one or more surfaces via a probe. In other embodiments (and as illustrated in FIGS. 6, 7 and 9), the RCA products may be immobilized in cells or on the one or more surfaces via a probe.

The sequences of the pairs of sequences identified in (d) can be used to make one or more physical maps (which may comprise overlapping and/or non-overlapping maps) of the immobilized RCA products, where the maps provide the locations of the immobilized RCA products in the cells or on the one or more surfaces, e.g., of cells. As noted above, depending on how the method is implemented the map may be a two dimensional or three-dimensional map.

As will be described in greater detail below, the RCA products can be immobilized to via one or more binding agents (e.g., antibodies), wherein the binding agents are each bound to (i.e., hybridized to) a sequence in an RCA product and as well as a site in or on a cell (e.g., a cell surface marker). In these embodiments, the method may further comprise performing a proximity assay between the one or more binding agents and the RCA product to which they are bound, thereby allowing the binding agents on the surface to be mapped to a particular RCA product.

Once the binding agents have been mapped to a particular RCA product, the location and quantity of individual binding agents can be mapped onto the physical map of the immobilized RCA products, as discussed above. The distribution of the binding agents on the map and the sites to which they are abound can be analyzed.

Also provided is a probe system. In some embodiments the probe system may comprise (a) a population of RCA products wherein the RCA products of the population of RCA products each have a unique RCA product identifier sequence and a grid oligonucleotide binding sequence; and (b) a population of grid oligonucleotide molecules, wherein the sequence at the terminus at one end of the grid oligonucleotide molecules is complementary to a grid oligonucleotide binding sequence and the sequence at the terminus of other end of the grid oligonucleotide molecules is complementary to a grid oligonucleotide binding sequence, wherein hybridization of (a) and (b) produces a complex in which the grid oligonucleotides hybridize to adjacent RCA products. The grid oligonucleotide molecules may be single molecules (where the nucleotides are covalently linked to each other) or split into one or more sequences. In these embodiments, if the grid oligonucleotide molecules are split into one or more sequences then the system may further comprise one or more splint oligonucleotides that hold the sequences together.

In some embodiments the probe system may comprise: (a) a population of RCA products, comprising: (i) a first set of RCA products each comprising a repeated sequence comprising a unique RCA product identifier sequence and a first grid oligonucleotide binding sequence; and (ii) a second set of RCA products comprising a repeated sequence comprising a unique RCA product identifier sequence and a second grid oligonucleotide binding sequence; (b) a population of grid oligonucleotide molecules, wherein the sequence at the terminus at one end of the grid oligonucleotide molecules is complementary to the first grid oligonucleotide binding sequence and the sequence at the terminus of other end of the grid oligonucleotide molecules is complementary to the second grid oligonucleotide binding sequence. In these embodiments, hybridization of (a) and (b) produces a complex in which the grid oligonucleotides hybridize to adjacent RCA products.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
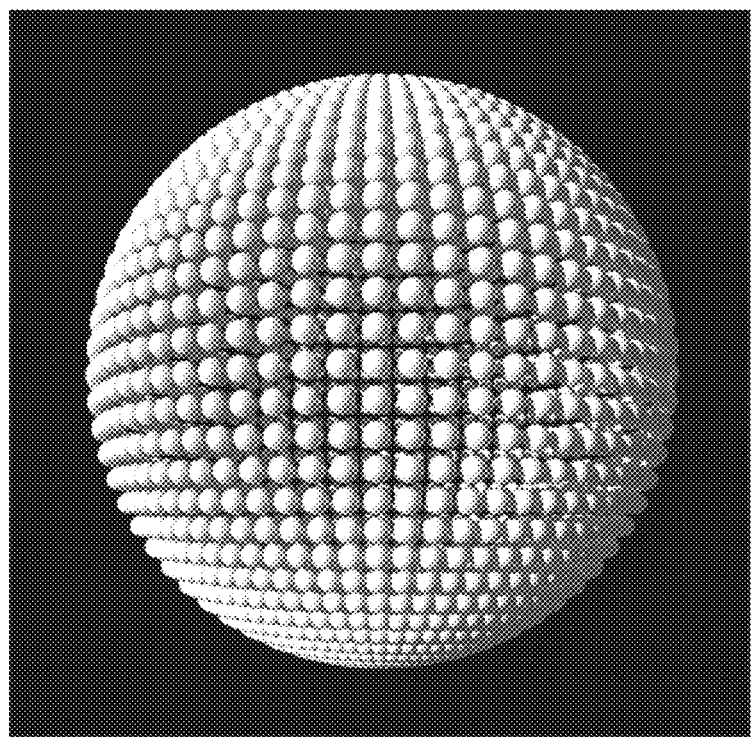
FIG. 1 schematically illustrates a cell covered in RCA products.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N. Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "primer" as used herein refers to an oligonucleotide that is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence or fragment, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by, e.g., Illumina, Life Technologies, BGI Genomics (Complete Genomics technology), and Roche etc. Next-generation sequencing methods may also include nanopore sequencing methods or electronic-detection based methods such as, e.g., Ion Torrent technology commercialized by Life Technologies.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to forms of measurement, and include determining if an element is present or not. These terms include both quantitative and/or qualitative determinations. Assessing may be relative or absolute.

The term "ligating", as used herein, refers to the enzymatically catalyzed joining of the terminal nucleotide at the 5' end of a first DNA molecule to the terminal nucleotide at the 3' end of a second DNA molecule.

The terms "plurality", "set" and "population" are used interchangeably to refer to something that contains at least 2 members. In certain cases, a plurality may have at least 10, at least 100, at least 100, at least 10,000, or at least 100,000 members.

A "primer binding site" refers to a site to which an oligonucleotide hybridizes in a target polynucleotide or fragment. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

The term "extending", as used herein, refers to the extension of a primer by the addition of nucleotides using a polymerase. If a primer that is annealed to a nucleic acid is extended, the nucleic acid acts as a template for an extension reaction.

As used herein, the term "rolling circle amplification" or "RCA" for short refers to an isothermal amplification that generates linear concatemerized copies of a circular nucleic acid template using a strand-displacing polymerase. RCA is well known in the molecular biology arts and is described in a variety of publications including, but not limited to Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993) and Schweitzer et al (Curr. Opin. Biotech 2001 12:21-27), which are incorporated by reference herein.

As used herein, the term "rolling circle amplification products" refers to the concatemerized products of a rolling circle amplification reaction. As used herein, the term "fluorescently labeled rolling circle amplification products" refers to rolling circle amplification products that have been fluorescently labeled by, e.g., hybridizing a fluorescently labeled oligonucleotide to the rolling circle amplification products or other means (e.g., by incorporating a fluorescent nucleotide into the product during amplification).

As used herein, the term "surface" refers to any solid material (e.g. glass, metal, ceramics, organic polymer surface or gel) that may contains cells or any combinations of biomolecules derived from cells, such as proteins, nucleic acids, lipids, oligo/polysaccharides, biomolecule complexes, cellular organelles, cellular debris or excretions (exosomes, microvesicles), etc. Tissue blots, western blots and glass slides are examples of solid materials that have a surface. Cells, e.g., suspensions of mammalian cells, are another example of a surface.

As used herein, the term "splint" refers to an oligonucleotide that hybridize to the ends of two other oligonucleotides and brings those ends together to produce a ligatable junction. Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

The following disclosure provides a way to map adjacent RCA products. The map produced by the method may be a three-dimensional map or a two-dimensional map, depending on how the method is implemented. For example, if the RCA products are immobilized within cells (e.g., produced in situ in cells) then the map produced may be three dimensional. In other embodiments, e.g., if the RCA products are immobilized on one or more surfaces (e.g., the surface of one or more cells that may be in suspension or mounted on a support), then the map produced by the method may be two dimensional. While the method can be applied to cells (as described below) the method can be adapted to map adjacent RCA products that are immobilized on any surface, e.g., a glass slide that may have a tissue blot, or a western blot, etc. Likewise, although the RCA products or the grid oligonucleotide molecules to which the RCA products may be bound can be anchored to sites in or cell or on a surface via an antibody (e.g., an antibody that is conjugated to an oligonucleotide that has a sequence that is complementary to a sequence in the RCA products or grid oligonucleotide molecules), the RCA products or grid oligonucleotide molecules can be immobilized via using any type of interaction, e.g., covalent or non-covalent interactions, directly or indirectly. For example, in some embodiments, the RCA products or grid oligonucleotide molecules may be bound to the cell via a binding agent (e.g., an aptamer, an antibody or an oligonucleotide, etc.), where the binding agent binds to a sequence in an RCA product or grid oligonucleotide molecule and a site in a cell or on the surface of the one or more cells. In some embodiments, the RCA products or grid oligonucleotide molecules may be immobilized via hybridization to an oligonucleotide that also hybridizes to a nucleic acid (e.g., to a cellular RNA) or the RCA products may be immobilized non-covalently to a site via an electrostatic interactions, via a streptavidin/biotin interaction, or by a covalent linkage (e.g., via a click coupling).

Figure 6:
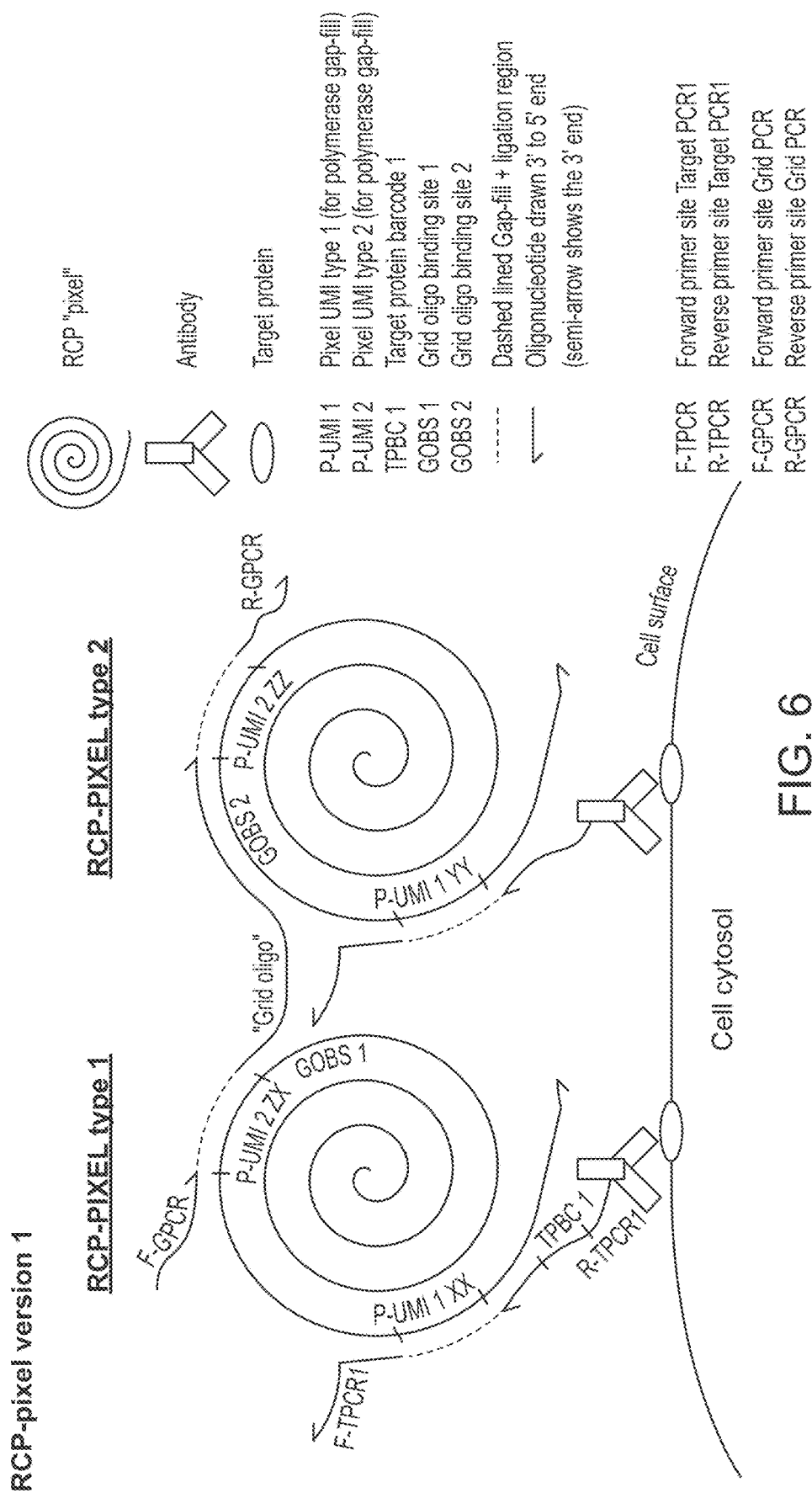
FIG. 6 schematically illustrates a first implementation of the present method.
Figure 7:
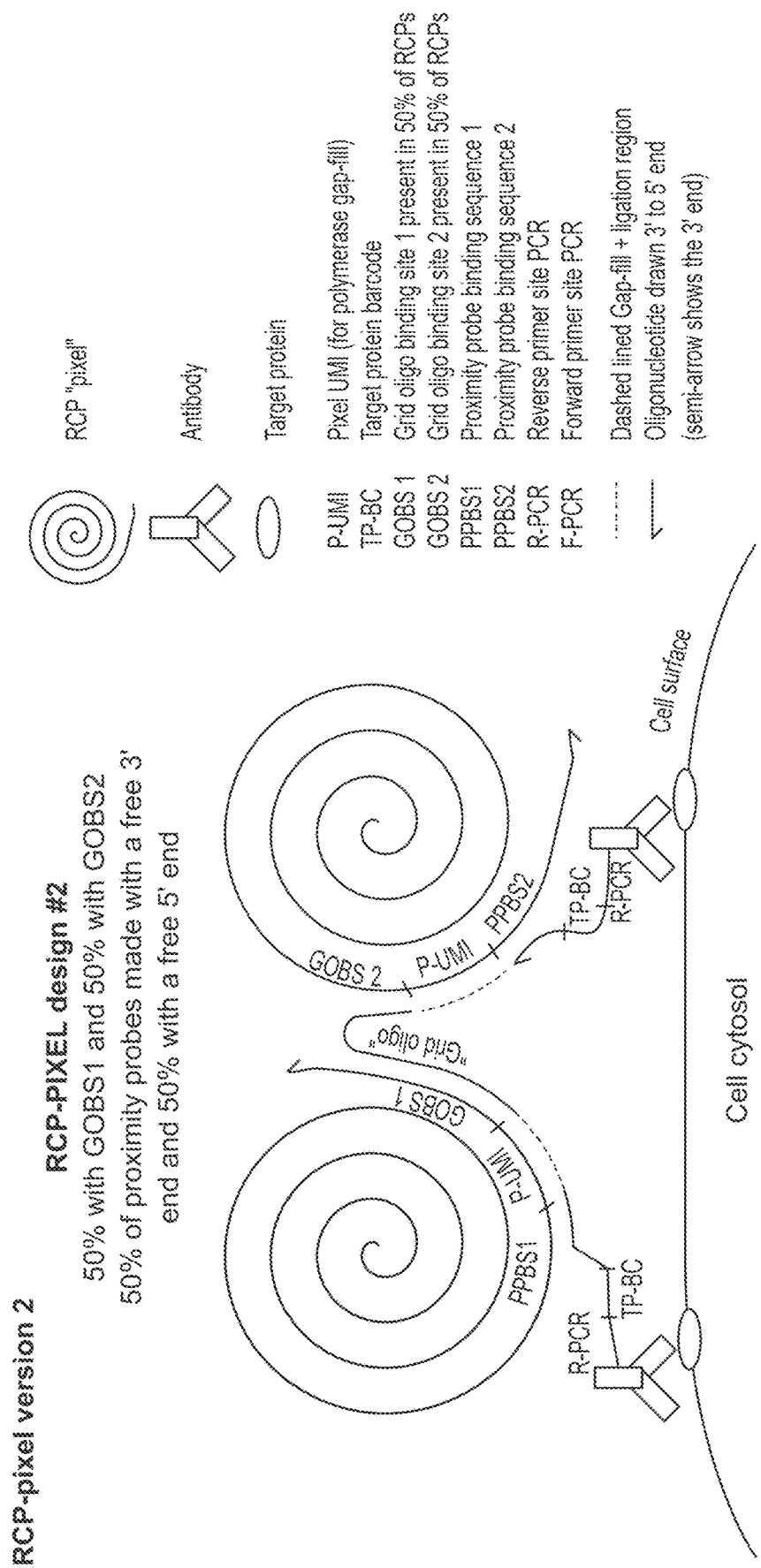
FIG. 7 schematically illustrates a second implementation of the present method.
Figure 9:
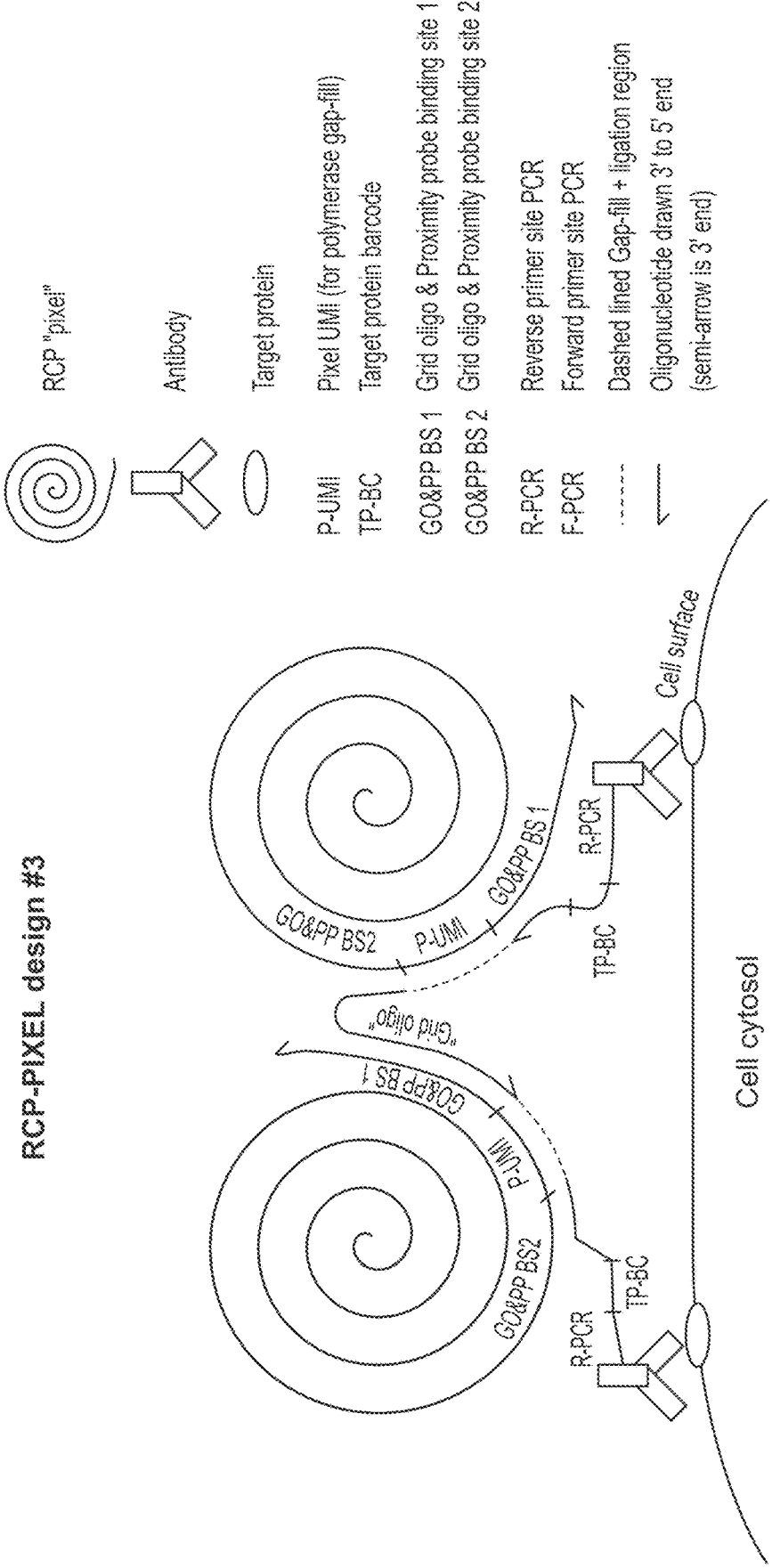
FIG. 9 schematically illustrates a third implementation of the present method.

For the sake of clarity, the phrase "hybridizing a population of grid oligonucleotide molecules with a population of RCA products, wherein either the grid oligonucleotide molecules or the RCA products are immobilized" is intended to cover implementations where either: (a) the grid oligonucleotides are hybridized to immobilized RCA products (in which case the RCA products are immobilized or produced in situ first, before the grid oligonucleotides are hybridized), as illustrated in FIGS. 6, 7 and 9, or (b) the RCA products are hybridized to immobilized grid oligonucleotides (in which case the grid oligonucleotides are immobilized or produced in situ first, before the RCA products are hybridized), as illustrated in FIGS. 10-12 and 14-16.

In any embodiment, the RCA products or grid oligonucleotide molecules may be immobilized in or on cells that are in solution, cells that are one on a support (e.g., a slide), cells that in a three-dimensional sample of tissue, or cells that in a tissue section. A sample containing cells that are in solution may be a sample of cultured cells that have been grown as a cell suspension, for example. In other embodiments, disassociated cells (which cells may have been produced by disassociating cultured cells or cells that are in a solid tissue, e.g., a soft tissue such as liver of spleen, using trypsin or the like) may be used. In particular embodiments, the RCA products may be immobilized on cells that can be found in blood, e.g., cells that in whole blood or a sub-population of cells thereof. Sub-populations of cells in whole blood include platelets, red blood cells (erythrocytes), platelets and white blood cells (i.e., peripheral blood leukocytes, which are made up of neutrophils, lymphocytes, eosinophils, basophils and monocytes). These five types of white blood cells can be further divided into two groups, granulocytes (which are also known as polymorphonuclear leukocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. If cells that are immobilized on a support are used, then then the sample may be made by, e.g., growing cells on a planar surface, depositing cells on a planar surface, e.g., by centrifugation, by cutting a three dimensional object that contains cells into sections and mounting the sections onto a planar surface, i.e., producing a tissue section. In alternative embodiments, the surface may be made by absorbing cellular components onto a surface.

Figure 10:
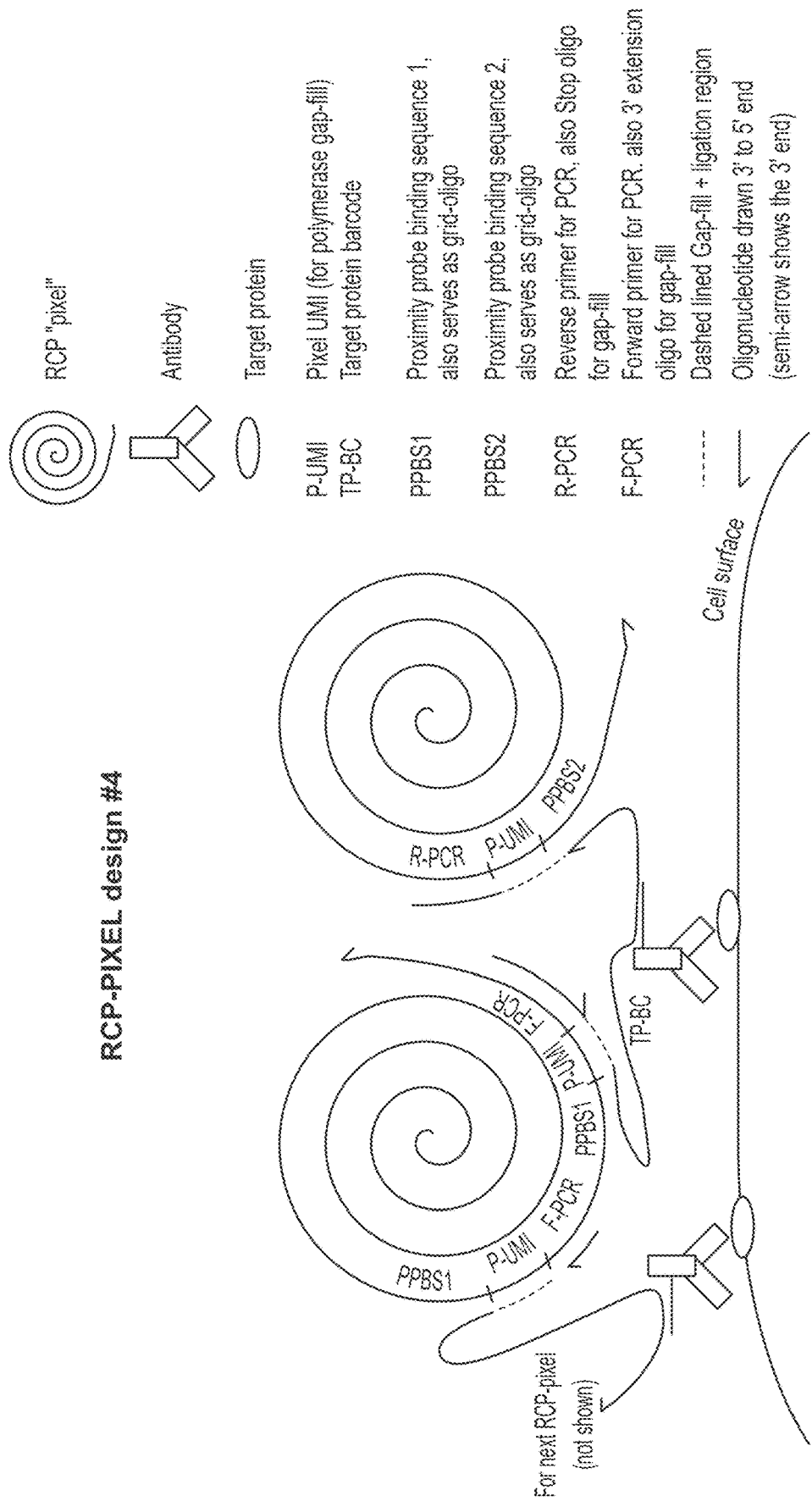
FIG. 10 schematically illustrates a fourth implementation of the present method.

In any embodiment, the method may comprise immobilizing thousands, tens of thousands, hundreds of thousands or at least a million RCA products (each having a unique identifier), to a population of cells (e.g., via an antibody) so that on each cell the RCA products coat the cells. A cell that is coated in RCA products is schematically illustrated in FIG. 1. As would be apparent, this figure is a schematic illustration; cells are not perfectly spherical and the RCA products are not perfectly spherical, the same size or evenly distributed in a regular pattern, as shown. RCA products may be anchored to the cells via an antibody, as illustrated in, e.g., FIGS. 6, 7, 9 and 10, or via a nucleic acid probe, as illustrated in, e.g., FIG. 11, although other methods are possible. In cases, the RCA products may be immobilized to the cell by hybridization to a grid oligonucleotide, as shown in FIG. 10. As will be described in greater detail below, each of the RCA products has unique identifier sequences as well as a sequence to which the grid oligonucleotides hybridize. The grid oligonucleotides and RCA products hybridize to produce a matrix comprising the RCA products and grid oligonucleotides, where the grid oligonucleotides are hybridized to adjacent RCA products. After hybridization, the unique identifier sequences of adjacent RCA products are copied from the RCA products onto the grid oligonucleotides. As will be described in greater detail below, the grid oligonucleotides can be sequenced. A physical map of the RCA products can be constructed based on the sequences that have been added to the grid oligonucleotides.

Figure 2:
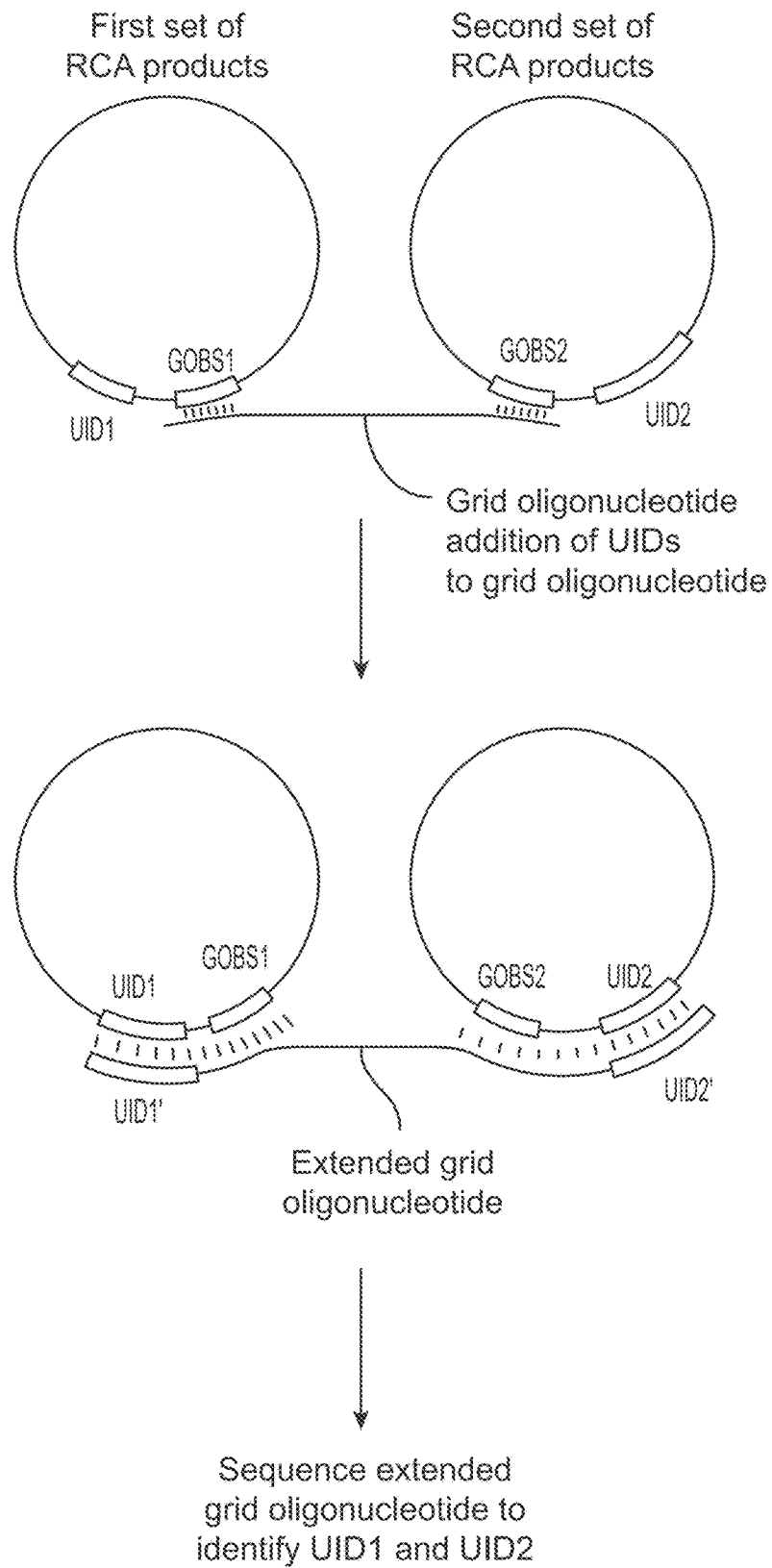
FIG. 2 schematically illustrates an example of how unique molecular identifiers from adjacent RCA products can be added to a grid oligonucleotide. In this example, the complement of one of the unique molecular identifiers (e.g., UID2) can be added onto the 3' end of a grid oligonucleotide by extending the 3' end of the grid oligonucleotide using an RCA product as a template and the complement of the other of the unique molecular identifiers (e.g., UID1) can be added onto the 5' end of a grid oligonucleotide by, e.g., by a gap-fill/ligation of a upstream oligonucleotide (as illustrated in FIG. 3 and described in greater detail below) or by ligation of the grid oligonucleotide to an oligonucleotide that is complementary to the unique molecular identifier and hybridized to the RCA product. In the latter embodiment, the RCA product acts as a splint for ligation.

As illustrated in FIG. 2, in the first step of the method a grid oligonucleotide 2 (i.e., a population of grid oligonucleotide molecules) and a population of RCA products may be hybridized, where the grid oligonucleotide or the RCA products may be immobilized on one or more cells. This step can be implemented using a single grid oligonucleotide (i.e., a population of grid oligonucleotide molecules that have the same sequence, with an optional degenerate, e.g., random, sequence in the middle of the grid oligonucleotide that might serve as a molecule identifier). As described in the examples section, this method may be implemented using a population of RCA products that are otherwise the same except for the unique identifier sequence. However, in other embodiments the method may be implemented using two or more types of RCA product that differ in at least the unique identifier sequence as well as their grid oligonucleotide binding sequence. This latter embodiment is illustrated in FIG. 2. In the illustrated embodiment, the population of RCA products comprises: i. a first set of RCA products 4 each comprising a repeated sequence comprising unique RCA product identifier sequence ("UID1", as illustrated) and a first grid oligonucleotide binding sequence ("GOBS1", as illustrated), and ii a second set of RCA products 6 comprising a repeated sequence comprising a unique RCA product identifier sequence "UID2", as illustrated and a second grid oligonucleotide binding sequence ("GOBS2", as illustrated). There may be at least 100, at least 1,000 or at least 10,000 RCA products in the first set and a similar number (i.e., at least 100, at least 1,000 or at least 10,000 RCA products in the second set, where each RCA product has a unique RCA product identifier sequence. The first and second sets of RCA products are interspersed with each other such that an RCA product from the first set is likely to be proximal to at least one, but sometimes two, three or four RCA products from the second set.

In FIG. 2 the RCA products are shown as circles. RCA products are compact, roughly spherical particles that typically have a diameter in the range of 0.1 to 1 um. If desired, the size of the RCA products used in the method can be reduced by the addition of a contraction oligonucleotide that hybridizes to two or more sites within each RCA product, which reduces the size of the RCA product. Smaller RCA products may increase the resolution of the map produced by the method. Contraction oligonucleotides are described in, e.g., Clausson, (Sci Rep. 2015; 5:12317). Illustration of the RCA products as a circle in FIG. 2 does not imply that the DNA of an RCA product is itself a circle, although RCA is done using a circular template.

The RCA product can be made by, e.g., synthesizing initial oligonucleotides that have a degenerate sequence, circularizing the initial oligonucleotides using a splint, and amplifying the circularized oligonucleotides by RCA. In some embodiments, the initial oligonucleotides may contain a degenerate (e.g., random) sequence of 6-10 nucleotides, or even more random nucleotides dependent on the number of unique RCA products required. Amplification of circularized oligonucleotides that have a degenerate sequence should produce a population of RCA products that each have a unique identifier (i.e., a sequence that is different from the other RCA products in the population). Methods for generating RCA products that have unique identifiers are described in Wu et al (Nat. Comm. 2019 10:3854) and US20160281134, for example, and are readily adapted for use herein. In some embodiments, the different oligonucleotides that are used to make the first and second sets of RCA products are made separately and then mixed together. In other embodiments, the different oligonucleotides may be made in parallel on a planar support in the form of an array and then cleaved from the array. Examples of such methods are described in, e.g., Cleary et al. (Nature Methods 2004 1:241-248) and LeProust et al. (Nucleic Acids Research 2010 38:2522-2540).

As shown in FIG. 2, the grid oligonucleotide molecules used in the method can each comprise a first terminal sequence that is complementary to the first grid oligonucleotide binding sequence (GOBS1) and a second terminal sequence that is complementary to the second grid oligonucleotide binding sequence (GOBS2). At least some of the grid oligonucleotide molecules hybridize to two adjacent RCA products via those sequences. FIG. 2 shows a grid oligonucleotide that is hybridized to two adjacent RCA products. Assuming that consecutive bases are distanced by approximately 0.3 nm, then a 100-mer grid oligonucleotide should, in theory, be able to stretch 30 nm, a 200-mer grid oligonucleotide should, in theory, be able to stretch 60 nm and a 500-mer grid oligonucleotide should, in theory, be able to stretch 150 nm. As such, the RCA products to which a molecule of grid oligonucleotide hybridizes to may be less than 100 nm apart or less than 50 nm apart.

In the next step of the method, the grid oligonucleotide molecules that are hybridized to two adjacent RCA products are extended to add the complements of the unique RCA product identifier sequences from two adjacent RCA products to ends of the grid oligonucleotide, thereby producing extended grid oligonucleotides 8. In the example shown in FIG. 2, UID1' (i.e., the complement of UID1) is added to one end of the grid oligonucleotide and UID2' (the complement of UID2) is added to the other end of the grid oligonucleotide. In some embodiments, the grid oligonucleotides may be extended using a gap fill/ligation reaction (see, e.g., Mignardi et al, Nucleic Acids Res. 2015 43: e151) that adds complements of the unique RCA product identifier sequences from the two adjacent RCA products to the grid oligonucleotide. In other embodiments, the addition may be done by ligation as mentioned above.

Figure 3:
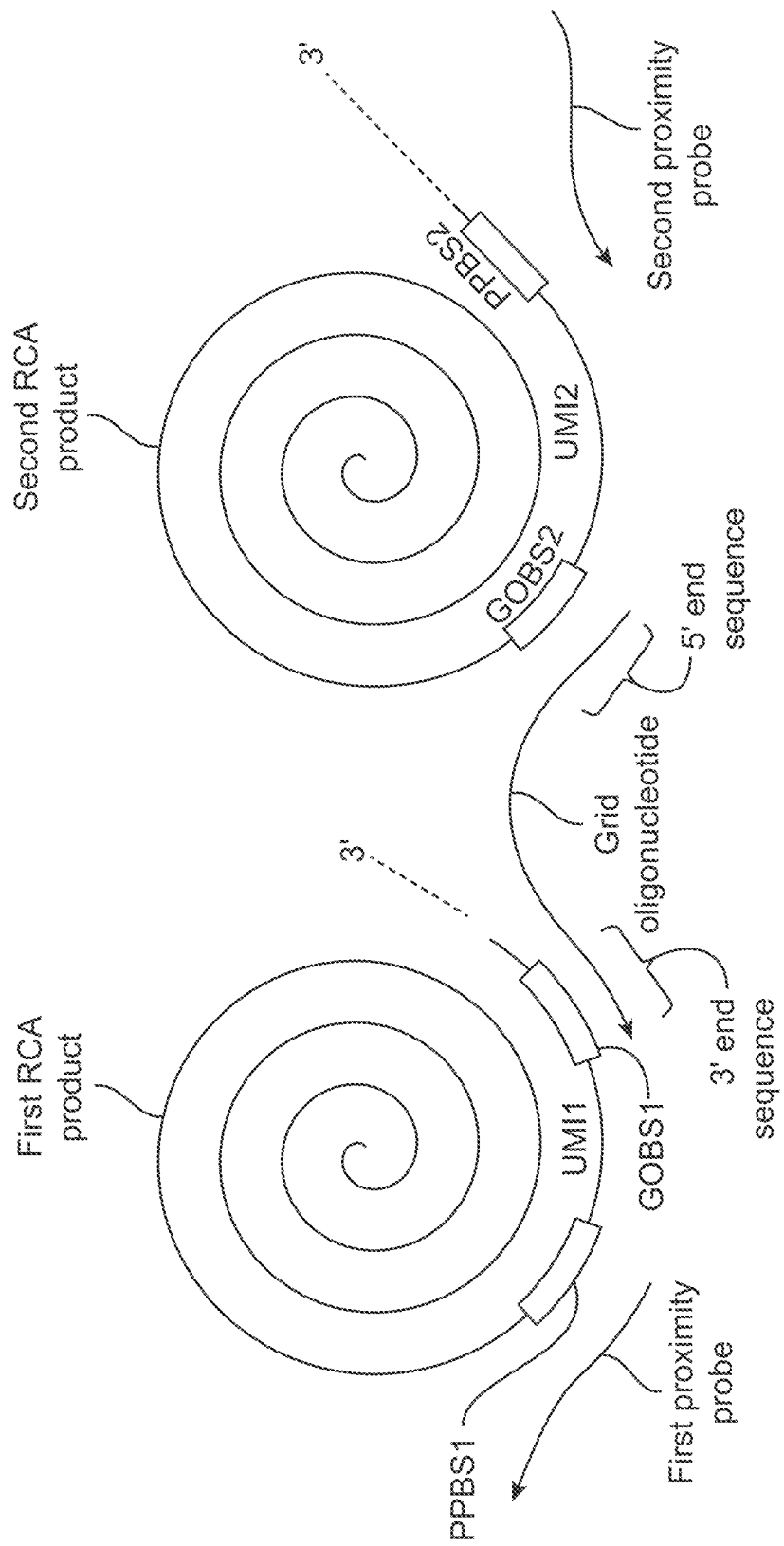
FIG. 3 schematically illustrates one way by which UMIs can be added to a grid oligonucleotide.

One method for adding the complements of the unique RCA product identifier sequences from the two adjacent RCA products to the grid oligonucleotide is illustrated in FIG. 3, although methods can be used. As shown in FIG. 3, the UID sequences may be added to the grid oligonucleotide using a system in which: (a) the first set of rolling circle amplification (RCA) products comprises at least a first type of RCA product that comprises a repeated sequence that comprises, in order from 5' to 3': a first proximity probe binding sequence (PPBS1, as shown), a first unique RCA product identifier sequence (UMI1, as shown) and a first grid oligonucleotide binding sequence (GOBS1, as shown); and (b) the second set of RCA products comprises at least a second first type RCA product that comprises a repeated sequence that comprises, in order from 5' to 3': a second grid oligonucleotide binding sequence (GOBS2, as shown), a second unique RCA product identifier sequence (UMI2, as shown) and a second proximity probe binding sequence (PPBS2, as shown). As shown in FIG. 3, the grid oligonucleotide used in this implementation has a 5' end sequence that is complementary to the second grid oligonucleotide binding sequence (GOBS2) and a 3' end sequence that is complementary to the first grid oligonucleotide binding sequence (GOBS1), upstream of the first unique RCA product identifier sequence. This implementation makes use of a first proximity probe that has a 5' end sequence that is complementary to the first proximity probe binding sequence (PPBS1); and the second proximity probe that has a 3' end sequence that is complementary to the second proximity probe binding sequence (PPBS2). As shown in FIG. 3, hybridization of these components together produces a complex in which the first and second unique RCA product identifier sequences can be copied by extending the 3' ends of the grid oligonucleotide and second proximity probe, respectively, via a gap-fill/ligation reaction. As would be apparent, in this embodiment, the first set of RCA products of may comprise at least 1000, at least 10,000, at least 100,000, at least 1M at least 10M, at least 100M, at least 1B, or at least 10B rolling circle amplification (RCA) products, wherein each RCA product in the first set comprises a repeated sequence that comprises, in order from 5' to 3': the first proximity probe binding sequence (PPBS1), a unique sequence that identifies the RCA product (UMI, as shown), and the first grid oligonucleotide binding sequence (GOBS1), and the second set of RCA products of (b) may comprise at least 1000, at least 10,000, at least 100,000, at least 1M at least 10M, at least 100M, at least 1B, or at least 10B rolling circle amplification (RCA) products, wherein each RCA product in the second set comprises a repeated sequence that comprises, in order from 5' to 3': the second grid oligonucleotide binding sequence (GOBS2), a unique sequence that identifies the RCA product (UMI, as shown), and the second proximity probe binding sequence (PPBS2).

As shown in FIG. 3, the UMIs may be added to the grid oligonucleotide in a reaction that involves: (a) producing a complex in which: (i) the 5' end of the first proximity probe is hybridized to the first proximity probe binding sequence (PPBS1) of the first RCA product; and (ii) the 3' end sequence of the second proximity probe is hybridized to the second proximity probe binding sequence (PPBS2) of the second set of RCA products, upstream of the unique sequences that identify the RCA products (UMI1 and UMI2, respectively); and (iii) the 3' and 5' end sequences of the grid oligonucleotide are hybridized to the first and second grid oligonucleotide binding sequences (GOBS1 and GOBS2) of the first and second RCA products, respectively; and (b) treating the complex of (a) with a polymerase and a ligase, thereby copying (via a gap-fill/ligation reaction) the complements of the first and second unique RCA product identifier sequences onto the 3' ends of the grid oligonucleotide and the second proximity probe, respectively, and producing a product molecule (an extended grid oligonucleotide) that comprises the complements of the first and second unique RCA product identifier sequences.

In these embodiments, the first and second sets of RCA products are interspersed with each other and immobilized on the cells, the 5' end sequence of the first proximity probe is hybridized to the first proximity probe binding sequence of the first set of RCA products, the 3' end sequence of the second proximity probe is hybridized to the second proximity probe binding sequence of the second set of RCA products, upstream of the unique sequences that identify the RCA products; and the 3' and 5' end sequences of the grid oligonucleotide are hybridized to the first and second grid oligonucleotide binding sequences of a pair of RCA products that are adjacent to one another. Again, treating the complexes with a polymerase, dNTPs and a ligase allows pairs of unique sequences that identify adjacent RCA products to be copied onto the ends of the grid oligonucleotide and the second proximity probe and results in product molecules (referred to herein as extended grid oligonucleotides) that comprise the complements of pairs of unique sequences that identify adjacent RCA products.

Figure 4:
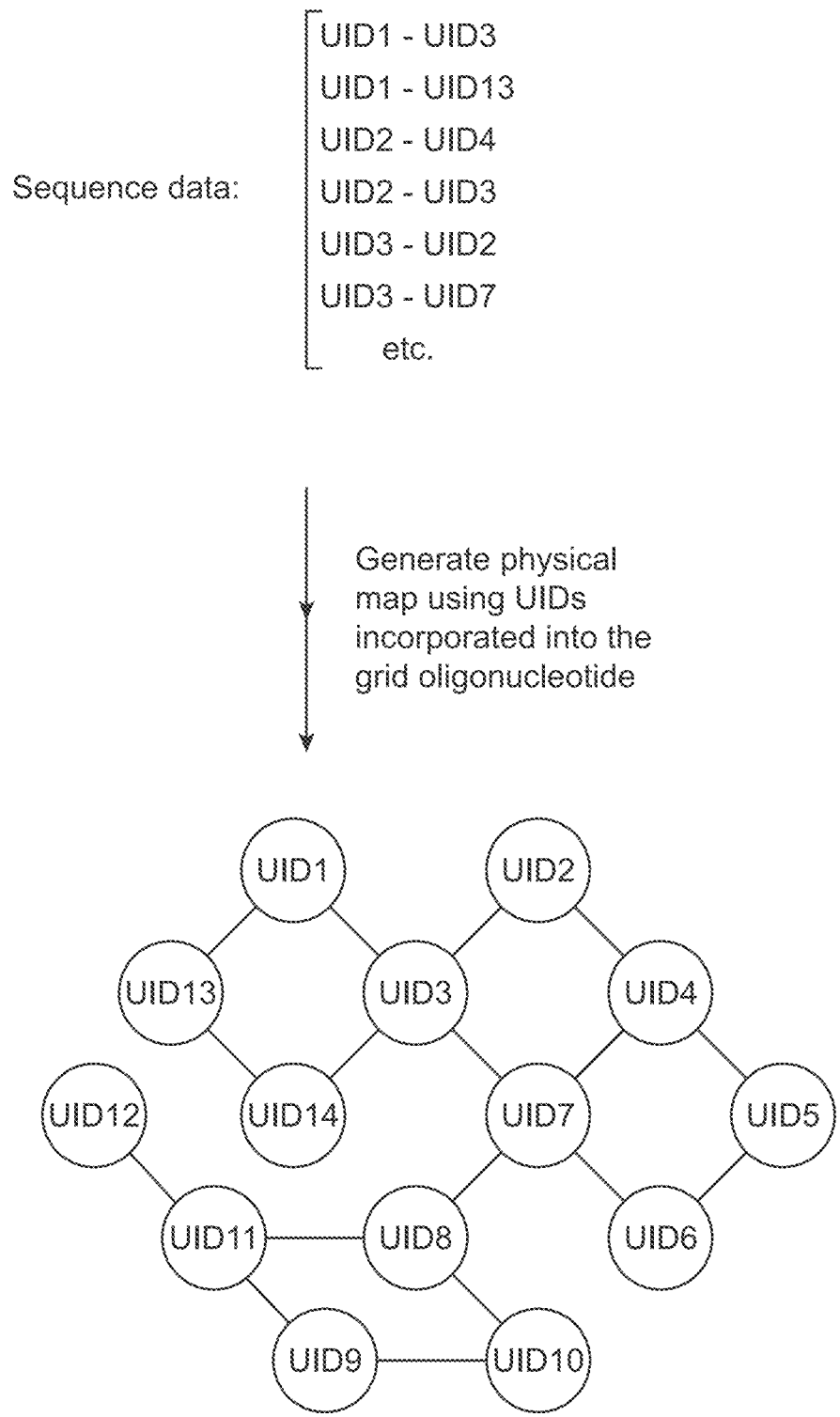
FIG. 4 schematically illustrates how the unique molecular identifiers that have been copied into the grid oligonucleotides can be mapped in a pairwise manner to produce a physical map of RCA products.
Figure 5:
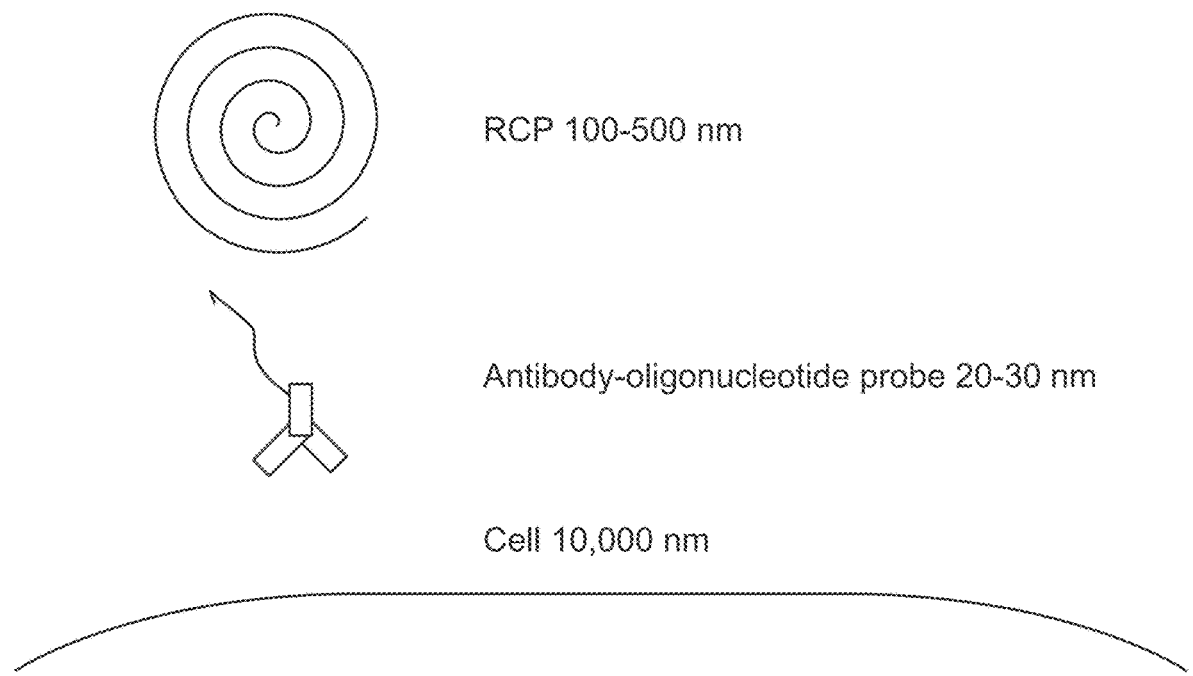
FIG. 5 schematically illustrates the relative sizes of UMI-tagged rolling circle amplification products, antibody-oligonucleotide probes and a cell.

As illustrated in FIG. 2, after the grid oligonucleotides have been extended to add the UIDs from adjacent RCA products onto their ends, the extended grid oligonucleotides 8 are sequenced and then analyzed to identify which pairs of unique RCA product identifier sequence complements have been added onto the grid oligonucleotides. This process is illustrated in FIG. 4. As illustrated in FIG. 4, each extended grid oligonucleotide should have the complement of a first unique RCA product identifier sequence at one end (e.g., UID1) and the complement of a first unique RCA product identifier sequence at the other (e.g., UID3). These sequences can be analyzed to compile a list of paired RCA product identifier sequence (e.g., UID1-UID3, UID1-UID13, etc.) which can be used to make a two-dimensional map of the RCA products that are on the surface of each cell. As illustrated in FIG. 4, the method may involve making one or more physical maps (a relational map) of the immobilized RCA products using the list paired RCA product identifier sequence of sequences. As would be apparent, the map may be a map of the surface of one or more cells. In some cases, the physical maps may comprise overlapping and/or non-overlapping maps.

In any embodiment, the extended grid oligonucleotides may be amplified by PCR prior to sequencing. In some of these embodiments, the binding sites for the PCR primers may be added to the 3' and 5' tails of first and second proximity probes, respectively, as illustrated in FIG. 3 or, in theory, the binding sites for the PCR primers could be coded into the RCA products and copied onto the ends of the grid oligonucleotides during the extension reaction.

Figure 11:
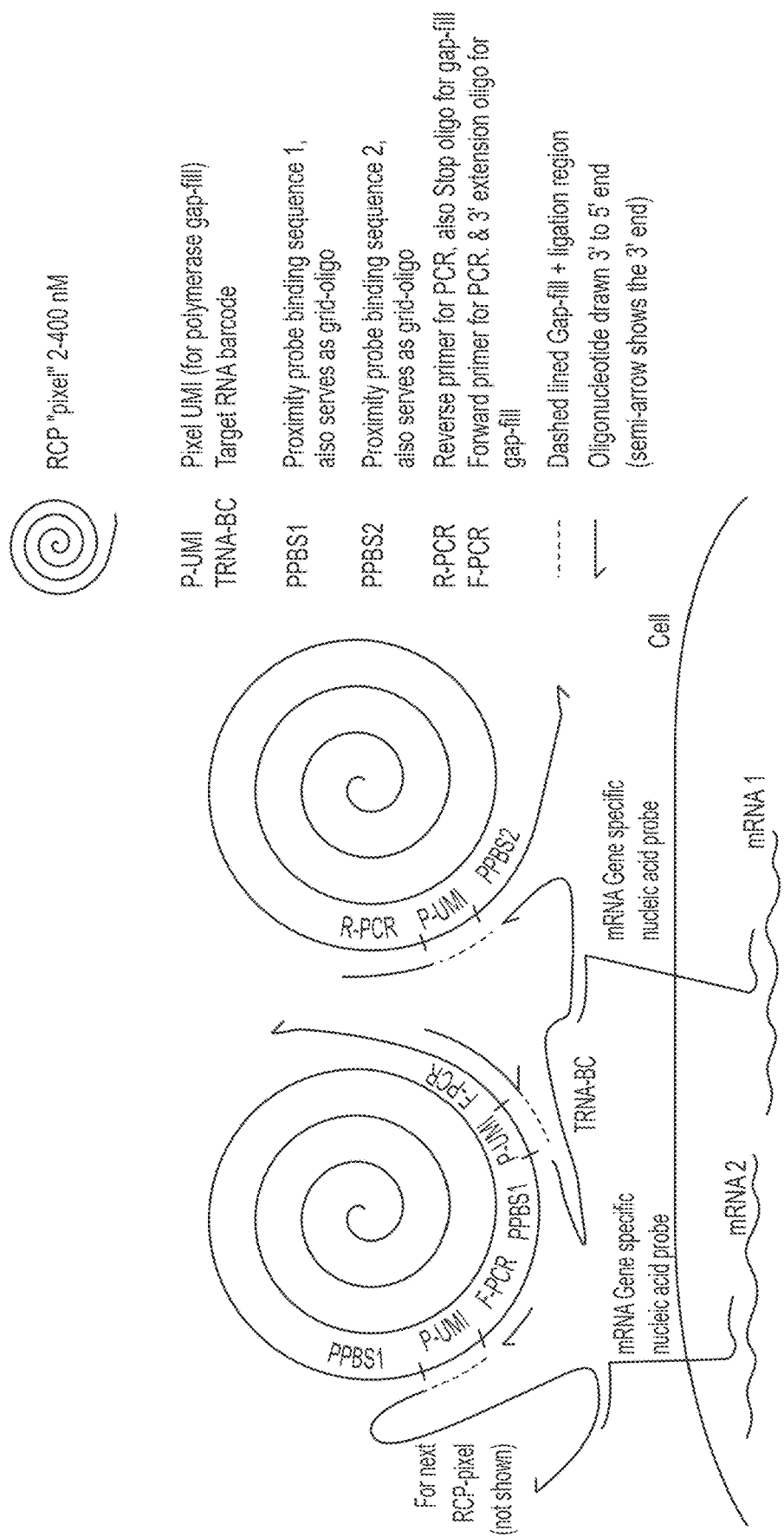
FIG. 11 schematically illustrates a fifth implementation of the present method.

In addition to making a map of the RCA products, the method may involve performing a proximity assay between one or more binding agents that are bound to sites in the cells or on the surface to the cells (e.g., antibodies that are bound to cell surface markers on the cells). In these embodiments, a unique RCA product identifier sequence may be copied into an oligonucleotide that is linked to the capture agent. In some embodiments, the capture agent is an antibody-oligonucleotide conjugate, as illustrated in FIGS. 6, 7, 9 and 10 and in other embodiments, the capture agent may be an oligonucleotide probe (as illustrated in FIG. 11). In these embodiments, the terms "antibody-oligonucleotide conjugate" and "capture agent that is linked to a oligonucleotide" refers to a capture agent, e.g., an antibody or aptamer, that is non-covalently (e.g., via a streptavidin/biotin interaction) or covalently (e.g., via a click reaction or the like) linked to a single-stranded oligonucleotide in a way that the capture agent can still bind to its binding site. The oligonucleotide and the capture agent may be linked via a number of different methods, including those that use maleimide or halogen-containing group, which are cysteine-reactive. The capture agent and the oligonucleotide may be linked proximal to or at the 5' end of the oligonucleotide, proximal to or at the 3' end of the oligonucleotide, or anywhere in-between. In some embodiments, the oligonucleotides may be linked to the capture agents by a linker that spaces the oligonucleotide from the capture agents. Oligonucleotides may be linked to capture agents using any convenient method (see, e.g., Gong et al., Bioconjugate Chem. 2016 27:217-225 and Kazane et al. Proc Natl Acad Sci 2012 109:3731-3736). In many embodiments, the sequence of an oligonucleotide that is conjugated to a binding agent uniquely identifies the epitope or sequence to which the binding agent binds. For example, if the method is performed using 10 different antibodies, then each antibody is tethered to a different sequence that identifies the epitope to which the antibody binds. This feature allows the method to be multiplexed and, in some embodiments, at least 5, at least 10, at least 20 or at least 50 different antibodies that bind to different markers in or on the surface of a cell can be used in the method. Each antibody is conjugated to a different antibody identifier sequence, and the antibody identifier sequences allow the binding events for a particular antibody to be mapped. Such tagged antibodies are described in, e.g., Wu et al (Nat. Comm. 2019 10:3854) and US20160281134, and others.

Figure 8:
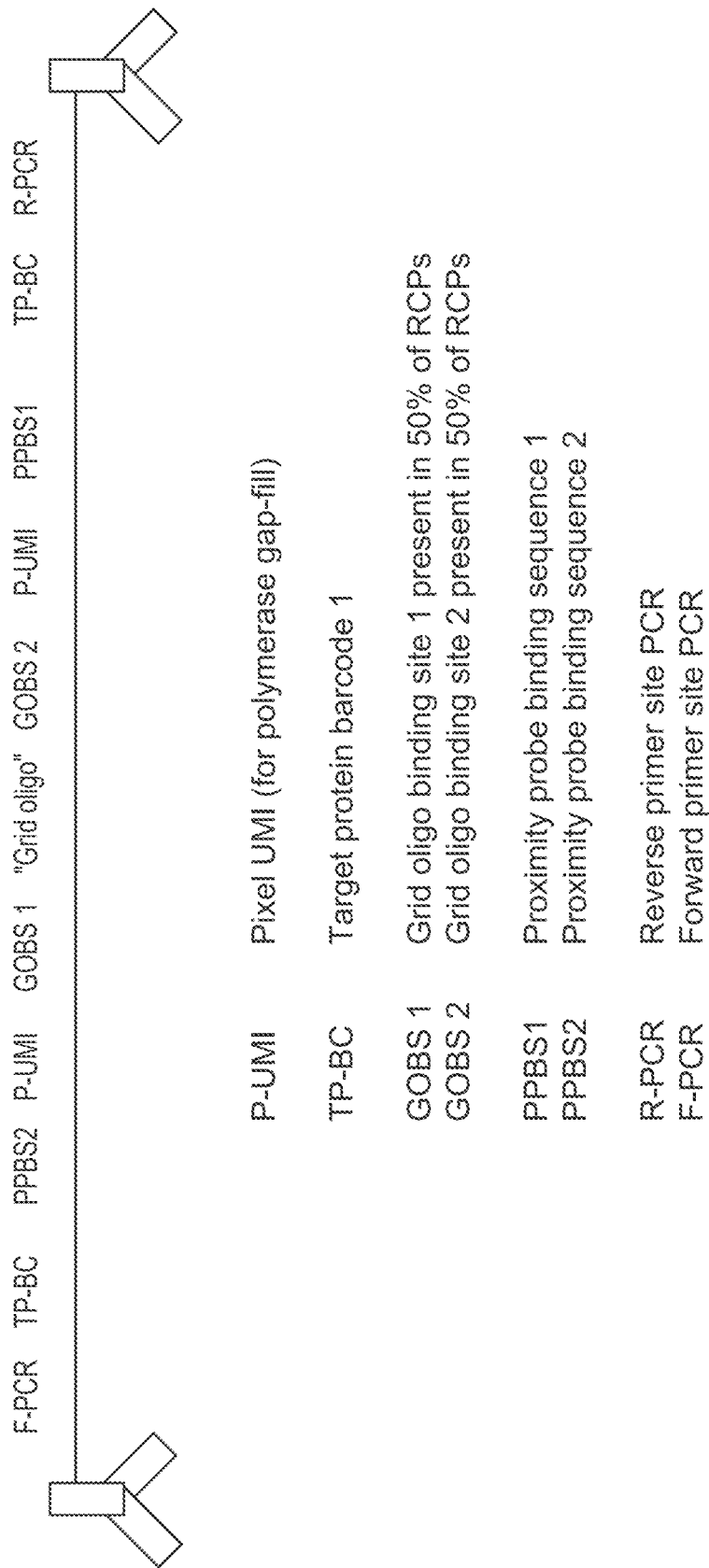
FIG. 8 schematically illustrates the PCR amplicons produced using the method shown in FIG. 7.

As illustrated in FIGS. 6, 7 and 9-16, the proximity assay may be implemented in a variety of different ways. In any embodiment, the proximity assay may produce products that contains the complement of a binding agent identifier sequence and the complement of a unique RCA product identifier sequence. In some embodiments, the product of the proximity assay (an extended proximity probe) may be a separate molecule to the extended grid oligonucleotide (as illustrated in FIG. 6). In other embodiments, the product of the proximity assay (an extended proximity probe) may be part of the extended grid oligonucleotide (see, e.g., FIGS. 7 and 9). In any embodiment, a portion of the capture agents used in the assay may be linked to the 5' ends of the oligonucleotides and the remainder of the capture agents may be linked to the 3' ends of the oligonucleotides (as illustrated in FIGS. 7 and 9). For example, in some embodiments, the method may make use of a mixture comprising one or more antibodies-oligonucleotide conjugates, where in some embodiments, some of the antibodies that bind to a particular cell surface marker (e.g., 30%-70% of the antibody molecules) are conjugated to the 5' end of an oligonucleotide and the remainder of the antibodies that bind to that cell surface marker are conjugated to the 3' and of an oligonucleotide. In these embodiments, the oligonucleotides may each contain a PCR primer binding site (at whichever end of the oligonucleotide that is linked to the antibody) and the product produced by the assay may be amplifiable by PCR, as illustrated in FIG. 8.

Figure 12:
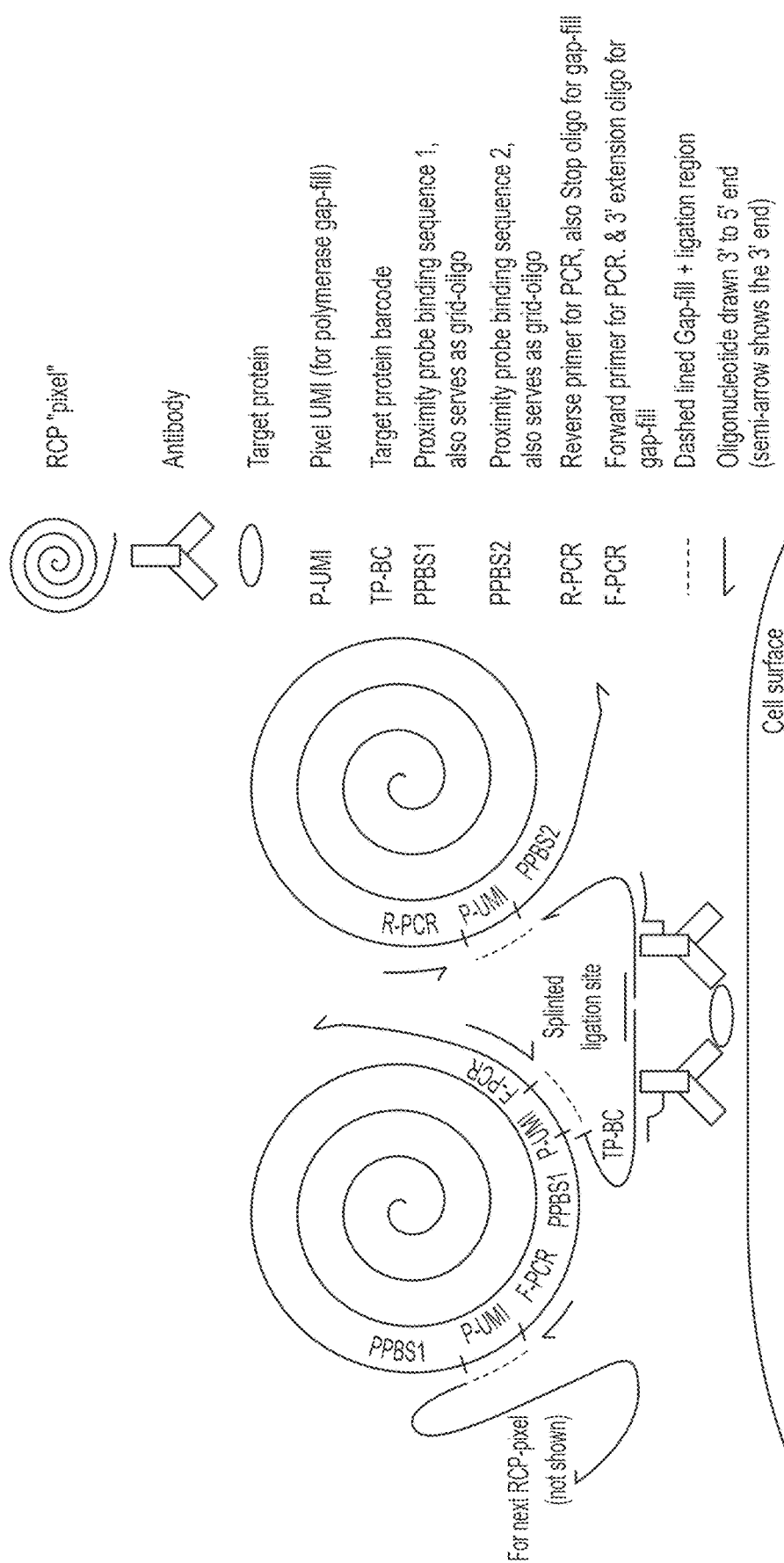
FIG. 12 schematically illustrates a sixth implementation of the present method.

As illustrated in FIGS. 10-16, in some embodiments, the grid oligonucleotide molecules may be immobilized to the surface of a cell prior to the addition of the RCA products. In these embodiments, the method may comprise (a) hybridizing a population of RCA products with a population of grid oligonucleotide molecules that are immobilized on one or more surfaces, wherein: (i) the RCA products of the population of RCA products each have a unique RCA product identifier sequence and a grid oligonucleotide binding sequence, and (ii) the grid oligonucleotide molecules each comprise a first terminal sequence that is complementary to a grid oligonucleotide binding sequence and a second terminal sequence that is complementary to a grid oligonucleotide binding sequence; and (iii) at least some of the grid oligonucleotide molecules hybridize to two adjacent RCA products; (b) extending the grid oligonucleotide molecules that are hybridized to two adjacent RCA products to add the complements of the unique RCA product identifier sequences from two adjacent RCA products to the grid oligonucleotide, thereby producing extended grid oligonucleotides; (c) sequencing the extended grid oligonucleotides; and (d) analyzing the sequences to identify which pairs of unique RCA product identifier sequence complements have been added onto the grid oligonucleotides. As shown in FIG. 12 in some embodiments, the grid oligonucleotide may, itself, be the product of a proximity ligation assay. In these embodiments, the grid oligonucleotides may be split such that each portion hybridizes to a different probe. In these embodiments, the intact grid oligonucleotide is only produced if the two parts of the grid oligonucleotide are proximal to each other and capable of ligating to one another in a splinted ligation reaction. As such, in some embodiments, the method may comprise making a physical map of the immobilized RCA products using the pairs of unique RCA identifier sequences identified by analysis of the sequence reads and, also, mapping the binding agents to the physical map of the immobilized RCA products by analyzing which unique RCA product identifier sequences and which binding agent identifier sequences are in the assay products. As shown in FIGS. 7 and 9, the complement of a binding agent identifier sequence and the complement of a unique RCA product identifier sequence can be incorporated into the extended grid oligonucleotide. In other embodiments, the complement of a binding agent identifier sequence and the complement of a unique RCA product identifier sequence are incorporated into assay products that are separate from the extended grid oligonucleotides. Analysis of the unique RCA product identifier sequence that are copied into the assay products in the proximity assay allows the binding sites for each of the capture agents that is bound to the cell to be mapped to a particular RCA product. Specifically, each binding event can be mapped to an RCA product because the unique RCA identifier sequence for that RCA product are added to binding agent-tethered oligonucleotides that are proximal to that RCA product. The binding agents can then be placed on the map of RCA products described above, thereby providing a two-dimensional map of the binding events, where the two dimensions correspond to the surfaces of one or more cells. Similar methods can be used to produce a two-dimensional map of the binding events.

As would be apparent, each RCA product contains multiple copies of the same sequence and, as such, multiple binding events can be mapped to a single RCA product, thereby providing a way to quantify the RCA products. For example, if a hundred antibody-oligonucleotide conjugates bind to sites that are all proximal to a particular RCA product, then all hundred binding sites can potentially be mapped to a single RCA product. Mapping binding sites to RCA products that, themselves, have been mapped in two dimensions provides a way to examine the distribution of binding sites in or on the surface of a cell. This, in turn, provides a way to examine cell polarity without microscopy.

Also provided herein is a probe system. In some embodiments, the probe system may comprise (a) a population of RCA products, comprising: (i) a first set of RCA products each comprising a repeated sequence comprising a unique RCA product identifier sequence and a first grid oligonucleotide binding sequence; and (ii) a second set of RCA products comprising a repeated sequence comprising a unique RCA product identifier sequence and a second grid oligonucleotide binding sequence; and (b) a population of grid oligonucleotide molecules, wherein the sequence at the terminus at one end of the grid oligonucleotide molecules is complementary to the first grid oligonucleotide binding sequence and the sequence at the terminus of other end of the grid oligonucleotide molecules is complementary to the second grid oligonucleotide binding sequence. As noted above, hybridization of (a) and (b) produces a complex in which the grid oligonucleotides hybridize to adjacent RCA products, as shown in FIG. 2. The first and second sets of RCA products each comprise at least 10 members (e.g., at least 100, at least 1,000, at least 1,000, at least 10,000, at least 100,000, at least 1M at least 10 M, at least 100 M, at least 1B or at least 10B) members. In some embodiments, the grid oligonucleotide binding sequences in the RCA products are adjacent to the unique RCA product identifier sequences in the RCA products, and the ends of the grid oligonucleotide molecules hybridize with the grid oligonucleotide binding sequences but not the unique RCA product identifier sequences. Further details of the probe system may be found in the methods section above.

Figure 13:
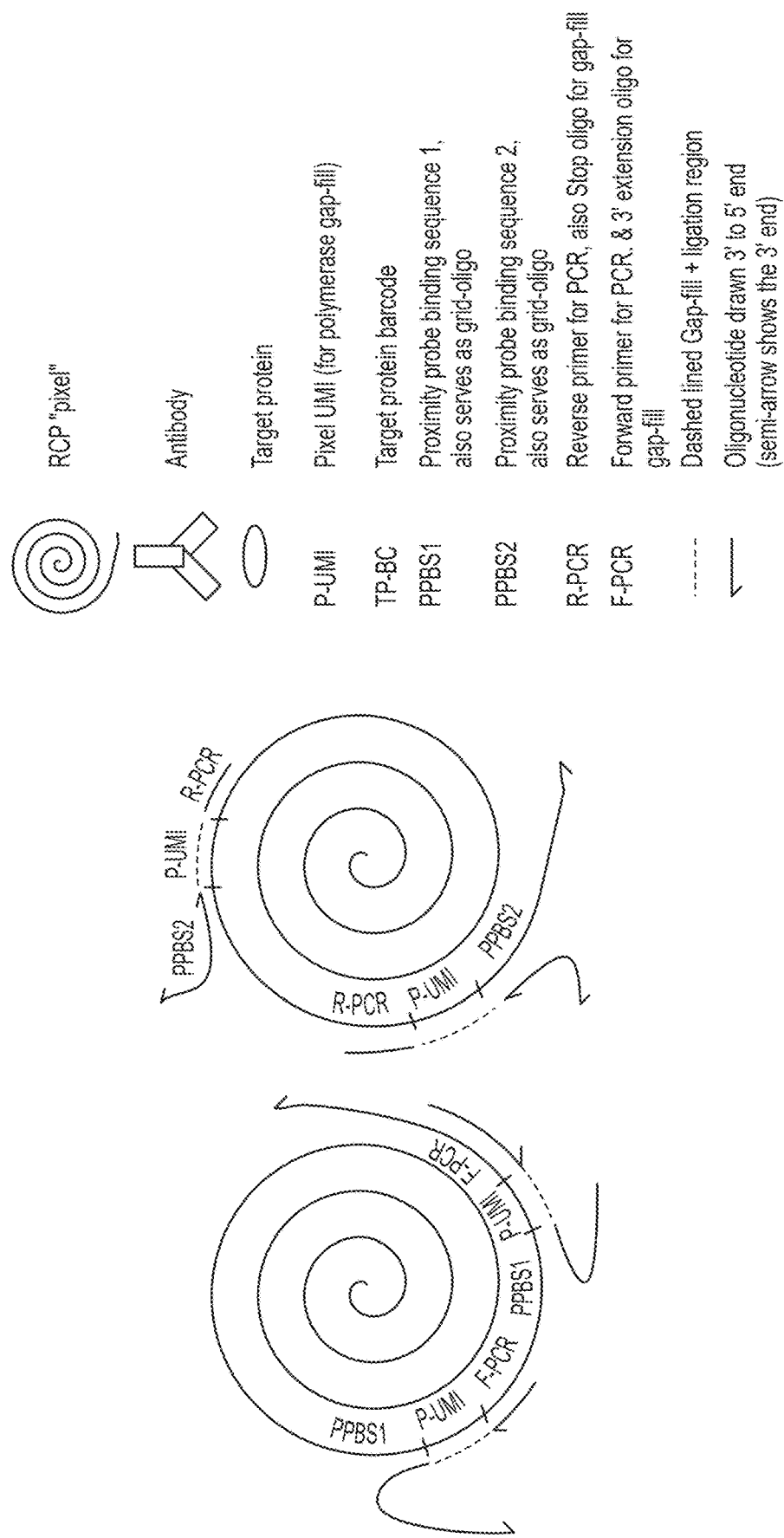
FIG. 13 schematically illustrates the first part of a seventh implementation of the present method.
Figure 14:
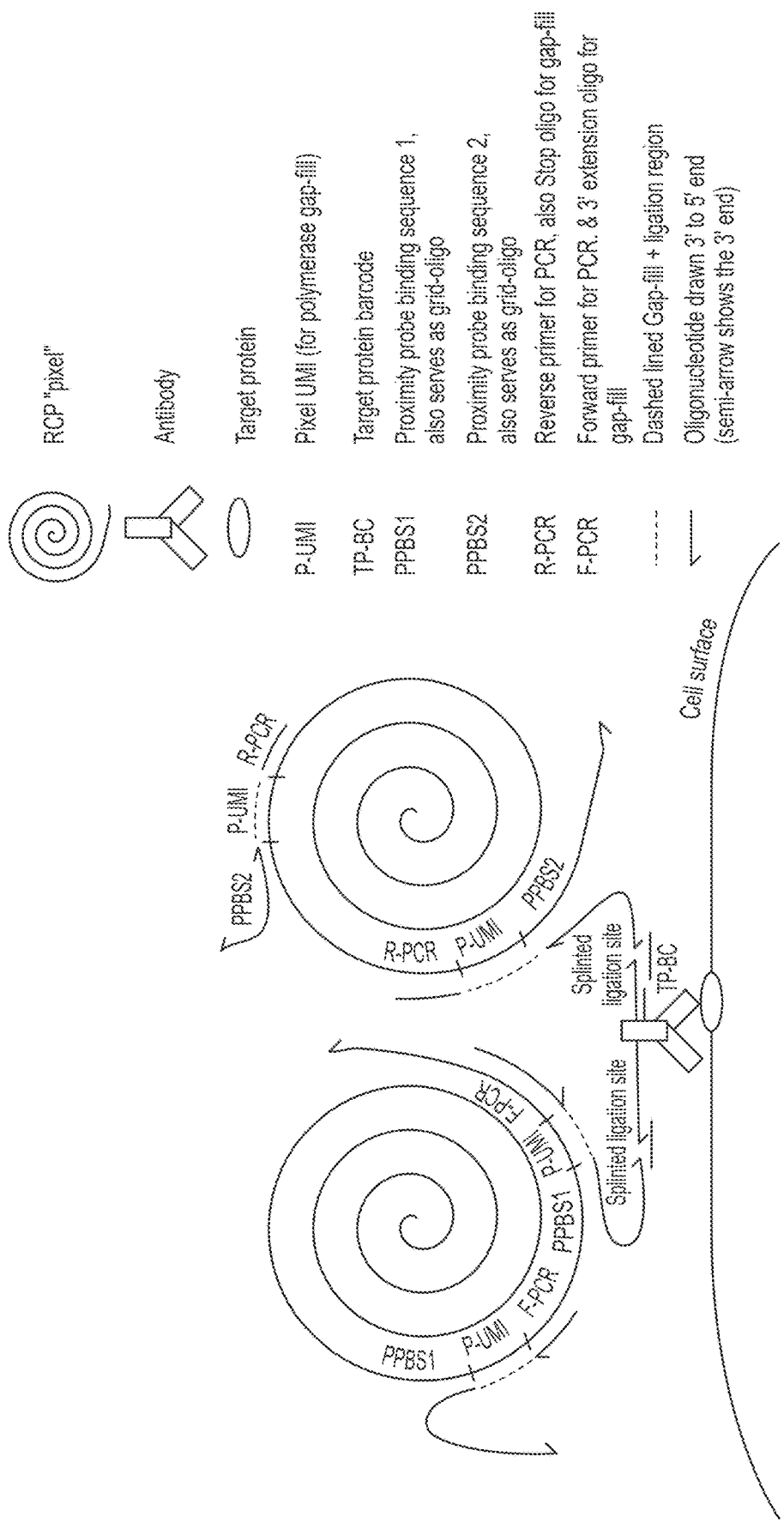
FIG. 14 schematically illustrates the second part of the seventh implementation of the present method.

Also provided is a population of RCA products that each have a unique RCA product identifier sequence, wherein at least some of unique RCA product identifier sequences in the RCA products are double-stranded and there are single strand regions gaps in between. An example of such a population is shown in FIG. 13. This population can be made by amplifying RCA templates as described above, denaturing the RCA products, hybridizing two or more oligonucleotides to the products, where one oligonucleotides hybridizes to a site that is upstream from the unique RCA product identifier sequences and another oligonucleotide hybridizes to a site that is downstream from the unique RCA product identifier sequences, and then linking the oligonucleotides via a gap-fill-ligation reaction. This seals the gap between the oligonucleotides and makes the unique RCA product identifier sequences in the RCA products are double-stranded. As shown, the ends of the double-stranded part of the products can be ligated to the grid oligonucleotides, as illustrated in FIG. 14.

Also provided is a population of RCA products comprising: a first set of RCA products each comprising a repeated sequence comprising a unique RCA product identifier sequence and a first grid oligonucleotide binding sequence (which is at least about 10, 12 or 15 nucleotides in length); and (ii) a second set of RCA products comprising a repeated sequence comprising a unique RCA product identifier sequence and a second grid oligonucleotide binding sequence (which is at least about 10, 12 or 15 nucleotides in length). In these embodiments, the grid oligonucleotide binding sequences in the RCA products may be adjacent to the unique RCA product identifier sequences. In any embodiment, the population of RCA products the first and second sets of RCA products each comprise at least 10, least 100, at least 1,000, at least 1,000, at least 10,000, at least 100,000, at least 1M at least 10 M, at least 100 M, at least 1B or at least 10B members.

Also provided by this disclosure are kits for practicing the subject methods, as described above. In certain embodiments, the kit may comprise the components of the probe system or starting products to make the products. The kit may additionally contain a ligase, nucleotides, a strand-displacing polymerase for performing rolling circle amplification and/or a polymerase for the gap-fill ligation reaction. The various components of the kit may be present in separate containers or certain compatible components may be pre-combined into a single container, as desired. In addition to the above-mentioned components, the subject kit may further include instructions for using the components of the kit to practice the subject method.

EMBODIMENTS

Embodiment 1. A method for identifying adjacent rolling circle amplification (RCA) products, comprising:
 (a) hybridizing a population of grid oligonucleotide molecules to a population of RCA products that are immobilized on one or more cells, wherein: (i) the RCA products of the population of RCA products each have a unique RCA product identifier sequence and a grid oligonucleotide binding sequence, and (ii) the grid oligonucleotide molecules each comprise a first terminal sequence that is complementary to a grid oligonucleotide binding sequence and a second terminal sequence that is complementary to a grid oligonucleotide binding sequence; and (iii) at least some of the grid oligonucleotide molecules hybridize to two adjacent RCA products;
 (b) extending the grid oligonucleotide molecules that are hybridized to two adjacent RCA products to add the complements of the unique RCA product identifier sequences from two adjacent RCA products to the grid oligonucleotide, thereby producing extended grid oligonucleotides;
 (c) sequencing the extended grid oligonucleotides; and
 (d) analyzing the sequences to identify which pairs of unique RCA product identifier sequence complements are have been added onto the grid oligonucleotides.

Embodiment 2. The method of embodiment 1, further comprising:
 (e) making one or more physical maps of the immobilized RCA products using the pairs of sequences identified in (d).

Embodiment 3. The method of embodiment any prior embodiment, wherein the extending comprises a gap fill and/or ligation reaction, which adds complements of the unique RCA product identifier sequences from the two adjacent RCA products to the grid oligonucleotide.

Embodiment 4. The method of embodiment 1, wherein in step (a):
 (i) the population of RCA products comprises: i. a first set of RCA products each comprising a repeated sequence comprising unique RCA product identifier sequence and a first grid oligonucleotide binding sequence, and ii a second set of RCA products comprising a repeated sequence comprising a unique RCA product identifier sequence and a second grid oligonucleotide binding sequence;

(ii) the grid oligonucleotide molecules each comprise a first terminal sequence that is complementary to the first grid oligonucleotide binding sequence and a second terminal sequence that is complementary to the second grid oligonucleotide binding sequence; and (iii) at least some of the grid oligonucleotide molecules hybridize to two adjacent RCA products.

Embodiment 5. The method of any prior embodiment, wherein the RCA products are immobilized to the cells via an antibody.

Embodiment 6. The method of any prior embodiment wherein the extended grid oligonucleotides are amplified by PCR prior to sequencing.

Embodiment 7. The method of any prior embodiment, wherein the RCA products are immobilized to the one or more cells via one or more binding agents, wherein the binding agents are each bound to a sequence in an RCA product and a site on the surface of the one or more cells.

Embodiment 8. The method of embodiment 7, further comprising performing a proximity assay between one or more binding agents and the RCA product to which they are bound.

Embodiment 9. The method of embodiment 8, wherein the proximity assay produces assay products that contains the complement of a binding agent identifier sequence and the complement of a unique RCA product identifier sequence.

Embodiment 10. The method of embodiment 9, wherein the method comprises:
(e) making a physical map of the immobilized RCA products using the pairs of sequences identified in (d); and mapping the binding agents to the physical map of the immobilized RCA products by analyzing which unique RCA product identifier sequences and which binding agent identifier sequences are in the assay products.

Embodiment 11. The method of embodiment 10, wherein the complement of a binding agent identifier sequence and the complement of a unique RCA product identifier sequence are incorporated into the extended grid oligonucleotides of step (b).

Embodiment 12. The method of embodiment 10, wherein the complement of a binding agent identifier sequence and the complement of a unique RCA product identifier sequence are incorporated into assay products that are separate from the extended grid oligonucleotides of step (b).

Embodiment 13. A probe system comprising:
(a) a population of RCA products wherein the RCA products of the population of RCA products each have a unique RCA product identifier sequence and a grid oligonucleotide binding sequence; and
(b) a population of grid oligonucleotide molecules, wherein the sequence at the terminus at one end of the grid oligonucleotide molecules is complementary to a grid oligonucleotide binding sequence and the sequence at the terminus of other end of the grid oligonucleotide molecules is complementary to a grid oligonucleotide binding sequence, wherein hybridization of (a) and (b) produces a complex in which the grid oligonucleotides hybridize to adjacent RCA products.

Embodiment 14. The probe system of embodiment 13 wherein: the population of RCA products of (a) comprises:
(i) a first set of RCA products each comprising a repeated sequence comprising a unique RCA product identifier sequence and a first grid oligonucleotide binding sequence; and (ii) a second set of RCA products comprising a repeated sequence comprising a unique RCA product identifier sequence and a second grid oligonucleotide binding sequence; and in the population of grid oligonucleotide molecules of (b) comprises, the sequence at the terminus at one end of the grid oligonucleotide molecules is complementary to the first grid oligonucleotide binding sequence and the sequence at the terminus of other end of the grid oligonucleotide molecules is complementary to the second grid oligonucleotide binding sequence.

Embodiment 15. The probe system of embodiment 14, wherein the first and second sets of RCA products each comprise at least 10 members.

Embodiment 16. The probe system of any of embodiments 13-15, wherein the grid oligonucleotide binding sequences in the RCA products are adjacent to the unique RCA product identifier sequences in the RCA products, and the ends of the grid oligonucleotide molecules hybridize with the grid oligonucleotide binding sequences but not the unique RCA product identifier sequences.

EXAMPLES

The following examples are put forth so as to provide those of ordinary skill in the art with additional disclosure and description of how to make and use the present invention, and are not intended to limit the scope of what the inventors regard as their invention nor are they intended to represent that the experiments below are all or the only experiments performed.

Example 1

The following example provides a way to analyze proteins and/or RNA in single cells without the need to compartmentalize single cells or microscopy. The method can be used to analyze cells in suspension, e.g., immune cells isolated from a body fluid, blood or a tissue, or fixed tissues or tissue sections that have been immobilized on a surface (e.g., a glass slide, for example). Such methods have traditionally used microscopy to image the cells. Here, the microscopy is eliminated and, instead, a binding pattern can be analyzed by DNA sequencing. In this method, the spatial relationships between the RCA products are determined to provide a map (in which each RCA product can be considered a "pixel") and the sites to which the capture agent binds are mapped to an RCA product. The method makes use of random barcoded (also called a "unique RCA product identifier sequence" or unique molecular identifier or "UMI") RCA products, which naturally condense into compact, approximately spherical shape having a diameter of a few hundred nm. The present method does not rely on proximal diffusion; rather the present method relies on grid oligonucleotides that hybridize adjacent RCA products.

Rolling circle replication products can be premade by circularization of multiple synthetic oligonucleotides carrying DNA sequences as tags. In the present method, a pool of rolling circle replication products (RCPs) consisting of at least millions of RCA products, each encoded with one or more random barcodes that identifies each RCA product. A 100 nucleotide DNA circle can be replicated by RCA into a concatemer of about 200 copies in 10 minutes using the phi-29 DNA polymerase (Wu et al Nature Comm. 2019 10:3854). The resulting RCA products will have a submicrometer size. If necessary, the pool of RCPs can be pre-sequenced in order to determine which UMIs are pairedup into one molecule in the case where more than one RCA product is used. In some cases, this information may be required in the final deconvolution of the data generated during analysis. One may also use only one random barcode per RCP depending on the molecular setup.

Target analyte proteins and/or RNA are bound by either a protein specific antibody linked to a DNA tag and/or RNA binding nucleic acid probe. Each analyte specific probe type carries a unique fixed and known (not random) bar code for target identification. These target specific probes have affinity for fixed Region 1 in the RCPs. The probes typically have a free 3' end for polymerase extension mediated by binding through hybridization to RCP Region 1. This gap-fill extension reaction is followed by a ligation event uniting the sequences that have been UMI encoded and are subsequently PCR amplified for high throughput DNA-sequencing.

All the RCA products also contain a fixed Region 2 which can hybridize to a so called "grid oligonucleotide". The grid oligonucleotide connects two nearby RCA products via hybridization thereby linking their random barcodes enabling the deconvolution of "pixel" location in relation to each other. Thereby finding which RCPs are close to each other.

Example 2

The following description provides a way to analyze a suspension of cells, e.g., lymphocytes.

The average lymphocyte has a volume of 130 um^3 and a surface area of about 124 um^2. The average diameter of an RCP is around 200 nm and an area of 0.12 um^2. This exemplary lymphocyte could have about 1000 RCPs covering it assuming a monolayer of RCPs on the surface of the cell.

$V=4/3pi\ r^3$ $A=pi^1/3 \times (6V)^2/3$

Thus, a typical cell is estimated to bind to about 1000 RCPs.

In this example, cells in suspension are analyzed also with a spatial resolution of target proteins on the surface of each single cell, possibly providing valuable diagnostic information. Such information is often called cell polarity and regulates many immune cell functions (Russel et al. Journal of Cell Science 2008 121:131-136 and Oliaro J. et al PNAS Dec. 5, 2006 103 (49) 18685-18690). Using presently available methods, the analysis of cell polarity requires microscopy to analyze the immune cells limiting the analytical throughput to a few cells and a few targets in just a few samples. The present method is capable of quantifying the abundance and relative positions of hundreds to thousands of cell surface markers on millions of immune cells. Cell polarity (namely the uneven distribution of cell surface proteins on a cell) regulates many important functions and is very difficult to analyze for many proteins on many cells. The polarization regulates not only cell migration but also immune cell activity for example antigen presentation and effector functions.

Example 3

Materials and Methods

Production of proximity probes. Antibodies (or other protein binders) are linked with a specific nucleic acid sequence either resulting in a free 3'-end, or a free 5'end, or even with both free 3' and 5'-ends. The covalent attachment of an oligonucleotide to an antibody can be done in many ways such as NHS-ester/maleimide chemistry to random lysines in an antibody. Other links can also be made through thiols or carbohydrates present on the antibodies. A proximity sequences can be linked directly to an antibody or via hybridization to another oligonucleotide that is linked covalently to the antibody (Lundberg et al. Nucleic Acids Research 2011 39: e1022011). Homo-bifunctional (such as BS3) or hetero-bifunctional (NHS-ester/maleimide) or click chemistry may also be used (Fredriksson et al 2007 Nature Methods 2007 4:327-329).

The sequences synthesized for coupling to the antibodies should contain a target protein identification bar-code sequence (i.e., a barcode sequence that is specific for the antibody). Some assay designs may also include the grid oligonucleotide sequence into the sequence coupled to the antibody (see FIG. 10). Multiple antibodies specific for a particular target protein will be functionalized with unique sequences. These will then be pooled for storage.

Production of RCA products. The rolling circle replication products used in this assay will be premade as unique molecules containing the random barcode (unique molecular identifier, UMI). These RCA products are made by first synthesizing a DNA oligonucleotide, or a pool of sequences cleaved from an array. These DNA molecules are then circularized by ligation after hybridization to a ligation DNA template (i.e., a "splint" that hybridizes to the ends of the oligonucleotide) and a DNA ligase enzyme. This circular molecule is then copied by rolling circle replication using a DNA polymerase and dNTPs. The polymerase may be phi29 DNA polymerase, but others may be used. The polymerization reaction is stopped by for example heating about 60 degrees and the pool of Pixel-RCPs are stored as a detection reagent for use in the assay.

The RCA products contain a concatemeric copy of the complement of the circularized template. Depending on the design, the RCA products may contain not only the UMIs but sequences for hybridization of the proximity probe sequences and the grid-oligos (as illustrated in some of the figures).

GAP-fill polymerization. During the assay the UMI sequences are copied by DNA-polymerization to become incorporated into the PCR amplicons for subsequent DNA sequencing. Gap-fill polymerization is accomplished by addition of dNTPs, a DNA polymerase and a DNA ligase to the reaction. T4 DNA polymerase and Klenow fragment are often used for this purpose as well as T4 DNA ligase to covalently seal the gap. The DNA polymerase used can be with or without 3'exonuclease activity but preferably without strand displacement activity as this would displace the oligonucleotide to which the GAP is to be closed. A combination of phusion DNA polymerase and Ampligase is also often used for Gap-fill reactions (Niedzicka et al Scientific Reports 2016 6:24051).

Example 4

A first implementation of the method is shown in FIG. 6. In this implementation of the method (and potentially others) in order for the Grid-oligo to bind to two proximal rolling circle amplification products (which are indicated as RCP-pixels in the figure), and not to one and the same rolling circle amplification product, rolling circle amplification products types are manufactured as at least two different types, shown as type 1 and type 2, which differ in their grid oligonucleotide binding sequence (GOBS). These sequences are illustrated shown as GOBS1 and GOBS2. This design alleviates potential competitive hybridization reactions that would otherwise lower the efficiency of detection.

In this method, all rolling circle amplification products may be sequenced beforehand to identify which pairs of UMIs are in each rolling circle amplification products. In this implementation of the method, the UMIs are from the adjacent rolling circle amplification products are added to the oligonucleotide by a gap-fill/ligation reaction to produce an extended grid oligonucleotide that has forward and reverse PCR primer sites at the ends. Likewise, the UMIs that are adjacent to the oligonucleotides that are conjugated to the antibodies are added to those oligonucleotides via a gap-fill/ligation reaction to produce an extended antibody oligonucleotide that also has forward and reverse PCR primer sites at the ends. The extended grid oligonucleotides and the antibody oligonucleotide can then be amplified and sequenced.

Sequencing the grid-PCR molecules identifies proximal RCA products that have been hybridized to the same grid oligonucleotide molecule and have become encoded by UMIs from the same two proximal RCP-pixels by the gap-fill DNA polymerization event that is followed by a ligation.

Example 5

A second implementation of the method is shown in FIG. 7. In this implementation of the method (and potentially others): 1) Target cells are bound by the proximity probes (antibodies coupled to oligonucleotides barcoded for target protein identity containing either free 3' ends or free 5'ends) or nucleic acid probes capable of binding to specific RNA sequences; 2) Pre-formed RCA products of at least two types are added to the sample and allowed to hybridize to the ends of the proximity probes via the "proximity probe binding sequences" (PPBS); 3) The grid oligonucleotide is added to the sample and allowed to hybridize to GOBS1 and GOBS2 of either RCA product type. Optional washing steps between step 1, 2, 3, can be carried out to remove unbound reagents. 5) Next, the method may comprise allowing a DNA polymerase and dNTPs to extend hybridized 3'-ends and a ligase to unite the sequence, thereby encoding a PCR amplicon with the UMIs from the RCA products to produce a target amplicon spanning from one proximity probe to another via two RCA products, which UMIs provides their relative location. As the RCA products have multiple copies of the same sequence many target proteins barcodes may be united with the same UMI to provide the location of multiple proteins in one area covered by that RCA product. As the product spans at least two RCA products, a grid of proximal RCPs can be obtained. 6) Next, the method comprises amplifying the united amplicon with PCR and then sequencing it to decode the image of which proteins are where.

As with example I, in order for the grid-oligonucleotide to bind to two proximal RCA products, and the same RCA product, at least two RCP-pixel types are manufactured that differ in their grid oligonucleotide binding sequence (GOBS1 and GOBS2). UMIs are encoded into from RCA product into the extended grid oligonucleotide.

FIG. 8 schematically illustrates the structure of an extended grid oligonucleotide in this implementation of the method.

Example 6

A third implementation of the method is shown in FIG. 9. In this implementation of the method: 1) the target cells are bound by the proximity probes (antibodies coupled to oligonucleotides barcoded for target protein identity containing either free 3' ends or free 5'ends) or nucleic acid probes capable of binding to specific RNA sequences. 2) Pre-formed RCA products of one type are added to the sample and allowed to hybridize to the ends of the proximity probes via the grid oligonucleotide and proximity probe binding sequences (GO&PP BS). As there is a surplus of GO&PP BS in the concatemeric Pixel-RCPs there will be binding sites left over for the Grid-oligo added in the next step; 3) The grid oligonucleotide is added to the sample and allowed to hybridize to GO&PP BS of the RCP-pixel. Optional washing steps may be performed between step 1, 2, 3, in order to remove unbound reagents. The next step may comprise 5) Allowing a DNA polymerase and dNTPs to extend hybridized 3'-ends and a ligase to unite the sequence to thereby encode a PCR amplicon with the Pixel-UMIs. This ligation produces a target amplicon spanning from one proximity probe to another via two RCA products, which provides their relative location. Because the RCA products have multiple copies of the same sequence, many target proteins barcodes can be united with the same UMI (from an RCA product) provide the location of multiple proteins in one area covered by that RCA product. Because the product spans at least two RCA products a grid of proximal RCA products can be obtained. 6) Next the method involves amplifying the united amplicon by PCR and then sequencing it to decode the image of which proteins are where. Again, the UMIs are encoded into from RCA product into the extended grid oligonucleotide.

Example 7

A fourth implementation of the method is shown in FIG. 10. In this implementation of the method: 1) the target cells are bound by the proximity probes (antibodies coupled to oligonucleotides barcoded for target protein identity containing either free 3' ends or free 5'ends) or nucleic acid probes capable of binding to specific RNA sequences; 2) Pre-formed RCA products of at least two types are added to the sample and allowed to hybridize to the ends of the proximity probes via the "proximity probe binding sequences" (PPBS); 3) the grid oligonucleotide is added to the sample and allowed to hybridize to GOBS1 and GOBS2 of either RCA product type. Optional washing steps may be performed between step 1, 2, 3, in order to remove unbound reagents; 5) next the method comprises allowing a DNA polymerase and dNTPs to extend hybridized 3'-ends and a ligase to unite the sequence to thereby encode a PCR amplicon with the UMIs from the RCA products, thereby forming a target amplicon spanning from one proximity probe to another via two RCA products to provide their relative location. As RCPs have multiple copies of the same sequence many target proteins barcodes are united with the same RCA product UMI providing the location of multiple proteins in one area covered by that RCA product. As the product spans at least two Pixel-RCPs a grid of proximal RCPs is obtained. 6) Next, the method comprises amplifying the united amplicon with PCR and then sequencing it to decode the image of which proteins are where. As with the examples above, in order for the grid oligonucleotide to bind to two proximal RCA products and not to the same RCA product, these RCA products are manufactured as at least two regions of differing sequences. In the embodiment shown, they differ in their GOBS sequence. Again, the UMIs are encoded into from RCA product into the extended grid oligonucleotide.

Example 8

The following example describes an implementation of the design shown in FIG. 10 ("design 4") and Example 7 as set forth above.

Antibody Bound Sequences

The target specific probe or antibody is to be linked to the following sequence via its free 3' end: 3' AAAAA-ATCCGCAGCTACGGCTAGGGCT 5' (SEQ ID NO: 1). The chemical coupling to an antibody can be achieved using a 3'-amine modification on the oligonucleotide, although several other chemistries could be used. The A-stretch is a flexible single stranded linker region, while the rest of the sequence hybridizes to target-barcode.

Grid Oligonucleotide

The grid oligonucleotide (or "bridge" oligonucleotide) contains a barcode that identifies the target to which the bridge grid oligonucleotide binds (i.e., "TP-BC") and first and second terminal sequences ("PPBS1" and "PPBS2") that are complementary to corresponding first and second grid oligonucleotide binding sequences in the RCA products. This oligonucleotide is hybridized to the antibody coupled sequence at a 1:1 ratio. The 6×A regions are flexible single stranded linkers. The middle region, TP-BC, is complementary the oligonucleotide that is linked to the antibody, thereby allowing the grid oligonucleotide to hybridize with the oligonucleotide that is linked to the antibody. The following sequence is an example of a grid oligonucleotide: 5' (PPBS1) P-TGAAGGTAGACGGAG-GATTTAT-AAAAAAA-TAGGCGTCGATGCC-GATCCCGA (TP-BC)-AAAAAAA-CAACATCAGTAT-TCCCAGGCTA (PPBS2)-3' (SEQ ID NO: 2).

RCA Product Manufacture and Use

In this example, the method uses two types of RCA products (which may be referred to "type 1" and "type 2" RCA products). As shown in FIG. 10, these products have a first grid oligonucleotide binding sequence (PPBS1) and one amplification primer binding site (F-PCR) or a second grid oligonucleotide binding sequence (PPBS2). These RCA products also have a unique RCA product identifier sequence, Nx22.

Type 1 RCA Products

The following oligonucleotide is circularized: 5'-P-TGGTTCGCAGGATGAG-GCCGGGAGTCTAACT-CAAATAC-NNNNNNNNNNNNNNNNNNNNNN-TGAAGGTAGACGGAGGATTTAT-CGCTTCGGTGAGATAG-3' (SEQ ID NO: 3) by hybridization to the ligation template oligonucleotide of sequence 5'-CTCATCCTGCGAACCA-CTATCT-CACCGAAGCG-3' (SEQ ID NO: 4), which acts as a circularization splint. The circularized oligonucleotide also contains the randomly generated UMI barcode "Nx22" as well as PPBS1 and the Forward PCR primer site (F-PCR"). The ligation template oligonucleotide for type 1 RCA products can also be used to prime the RCA reaction.

After amplification, the type 1 RCA product is a concatemer of the following sequence: 5'CTATCTCACCGAAGCG ATAAATCCTCCGTCTACCTTCA NNNNNNNNNNNNNNNNNNNNNN GTATTTGAGT-TAGACTCCCGGC CTCATCCTGCGAACCA-3' (SEQ ID NO: 5).

In this example, a primer that binds to F-PCR (of sequence GCCGGGAGTCTAACTCAAATAC; SEQ ID NO: 6) in the type 1 RCA product is extended, thereby copying the UMI in a gap-fill polymerization/ligation reaction. This reaction adds the complement of the UMI in the first RCA product to 5' end of the grid oligonucleotide.

Type 2 RCA Products

The following oligonucleotide is circularized: 5'-P-TAGTGAGTGTACGGAC CAACATCAGTAT-TCCCAGGCTA NNNNNNNNNNNNNNNNNNNNNN GTGCTGACCAATCGACCAAGAT CGCCTAGTCTC-TACTA-3' (SEQ ID NO: 7) by hybridization to the ligation template oligonucleotide of sequence 5-GTCCGTACACT-CACTATAGTAGAGACTAGGCG-3 (SEQ ID NO: 8), which acts as a circularization splint. The circularized oligonucleotide also contains the randomly generated UMI barcode "Nx22" as well as PPBS2 and the Reverse PCR primer site ("R-PCR"). The ligation template oligonucleotide for type 2 RCA products can also be used to prime the RCA reaction.

After amplification, the type 2 RCA product is a concatemer of the following sequence: 5'-TAGTAGA-GACTAGGCG-ATCTTGGTCGATTGGTCAGCAC-NNNNNNNNNNNNNNNNNNNNNN-TAGCCTGGGAATACTGATGTTG-GTCCGTACACTCACTA-3' (SEQ ID NO: 9).

In this example, the 3' end of the grid oligonucleotide hybridizes to its binding site in the type 2 product (PPBS2) and is extended, thereby copying the UMI in a gap-fill polymerization/ligation reaction. The 3' end of the grid oligonucleotide is extended until it meets the 5' end of an oligonucleotide of sequence 5'-P-GTGCTGAC-CAATCGACCAAGAT (SEQ ID NO: 10). The 3' end of this extension product ligates to the 5'-P end of the oligonucleotide.

PCR Amplification

The gap-fill polymerization/ligation reaction unites the grid oligonucleotide (and hence the TP-BC sequence) with the complements of two UMIs, one from a type 1 RCA product and the other from a type 1 RCA product. This product is amplified by PCR using the following primers: F-PCR primer 5'GTATTTGAGTTAGACTCCCGGC-3' (SEQ ID NO: 11) and R-PCR primer 5'ATCTTGGTCGAT-TGGTCAGCAC-3' (SEQ ID NO: 12).

The PCR product produced in this rejection will have the following sequences containing these elements: F-primer, Pixel-1 UMI, PPBS1, pA-linker, TP-BC, pA-linker, PPBS2, Pixel-2 UMI, R-primer. In this example, the product will have the sequence GCCGGGAGTCTAACTCAAATAC-Nx22-TGAAGGTAGACGGAGGATTTAT-AAAAAAA-TAGGCGTCGATGCCGATCCCGA-AAAAAAA-CAA-CATCAGTATTCCCAGGCTA-Nx22-GTGCTGACCAATCGACCAAGAT (SEQ ID NO: 13). The PCR amplification may contain additional Primer sequences useful for labeling each sample uniquely to enable downstream pooling of multiple samples prior to sequencing, so called sample barcoding.

Data Analysis

Once the resulting PCR product is clonally sequenced, the combinations of UMIs from the type 1 RCA products and the pixel RCA products (the complements of which been joined to the grid oligonucleotides), provides the relative location of each RCA product and can be used to produce a map of a surface area. The combinations of UMIs and the target barcode (TP-BC) provide the information of what target proteins (or mRNAs) are present in the very near vicinity (about 100 nm) of a given Pixel.

Assay Procedure

Cells on glass slides or in solution are may or may not be fixed prior to binding of the probes (mRNA binding probes and/or antibodies linked to nucleic acids). Cells are then may be blocked to reduce non-specific binding by addition of bulk non-specific antibodies and DNA such as salmon sperm DNA. Then probes are added to the sample typically done at low temperature over-night and then cells are washed to remove unbound probes. Then the RCP products are added, which hybridize to their respective binding sites in the probe sequences. Depending on the sequence design used, enzymes (ligases and polymerases) and dNTPs, ATP, and NAD and appropriate buffer conditions and temperature to allow the uniting of UMIs in the pixels including the target protein barcodes. Then the sample may be subjected to washing to remove the enzymes and co-factors and buffers to make room for PCR amplification components such as thermostable DNA polymerase and dNTPs and primers. After standard amplification the PCR product is processed to enable clonal amplicon sequencing at high throughput, as described above.

Example 9

A fifth implementation of the method is shown in FIG. 11. In this implementation of the method, RNA is detected. As shown, the grid oligonucleotide is designed to bind to a site in a probe that hybridizes with a cellular RNA. In this implementation, the sequencing results should show that mRNA 1 is proximal to mRNA 2 in the cell (since the grid oligonucleotides that are bound to those mRNAs (indirectly, via the probes) both add the UMI for the left hand RCA product when they are extended in the gap-fill/ligation reaction.

Example 10

A sixth implementation of the method is shown in FIG. 12. In this implementation of the method, the grid oligonucleotide is split into two parts, which only join together when they are in close proximity to one another in the presence of a splint. The implementation shown in in FIG. 12 is similar to the implantation described in Example 7 above (and shown in FIG. 10) except that a splint-mediated proximity ligation assay (PLA) step ensures that the grid oligonucleotide will be a single molecule if two binding events to the same target molecule occur. This increases the specificity of the assay. In this example, the grid oligonucleotide is split into two and splinted together by a PLA splint. The PLA splint can be designed to only splint proximity probe pairs that targeting the same protein, which further increases specificity and multiplexability.

Example 11

A seventh implementation of the method is shown in FIGS. 13 and 14. In this implementation of the method. FIG. 13 shows how the RCA products can be prepared. In this implementation, each of the two types of RCA products are pre-hybridized to two oligonucleotides, one upstream and one downstream of the UMIs. After the gap has been filled in by a gap-fill/ligation assay, the RCA products have multiple free 3' and/or 5' ends that can be added to the sample and allowed to interact with the target binding probes. As shown in FIG. 14, these RCA products (with free 3' and/or 5' ends that capable of ligation) are hybridized to a sample that is pre-hybridized with target-specific probes. In this embodiment, ligation reaction joins a gap-fill/ligation product on one RCA product to a gap-fill/ligation product on the other RCA product via the target-specific probe. The resulting product contain two pixel-derived UMIs as well as a barcode that indicates the specific target. One benefit of example 11, is that only an enzymatic ligation reaction is performed during the sample analysis simplifying the reaction but making the pre-preparation of RCA-products in bulk, somewhat more complicated.

Example 12

The following section describes an implementation of the general design shown in FIGS. 13 and 14 from Example 11 as set forth above.

Antibody Bound Sequences

The target specific probe or antibody is to be linked to the following sequence via its free 3' end: 3' AAAAA-ACCGTGGCCTGGCAGACTTTAC 5' (SEQ ID NO: 14). The chemical coupling to an antibody can be achieved using a 3'-amine modification on the oligonucleotide, although several other chemistries could be used. The A-stretch is a flexible single stranded linker region, while the rest of the sequence hybridizes to target-barcode.

Grid Oligonucleotide

The grid oligonucleotide is built in three parts united by ligation reactions during the assay step. Grid oligo part 1, 5' P-ACATAGGAGACAATTGAATAGC-AAAAAAA-TGGCACCGGACCGTCTGAAATG-AAAAAAA-AT-GAATTACGCGCGCTCAGACA-3' (SEQ ID NO: 15) binds by hybridization to the oligonucleotide covalently linked to the antibody and contains a barcode that identifies the target to which the antibody binds (i.e., "TP-BC"). This construction of the probe by hybridization is pre-prepared in bulk production.

RCA Product Manufacture and Use

In this example, the method uses two types of RCA products (which may be referred to "type 1" and "type 2" RCA products). As shown in FIG. 13, these products have a first grid oligonucleotide binding sequence (PPBS1) and one amplification primer binding site (F-PCR) or a second grid oligonucleotide binding sequence (PPBS2). These RCA products also have a unique RCA product identifier sequence, Nx22.

Type 1 RCA Products

The following oligonucleotide is circularized: 5'P-TGGTTCGCAGGATGAG-GCCGGGAGTCTAACT-CAAATAC-NNNNNNNNNNNNNNNNNNNNNN-TGAAGGTAGACGGAGGATTTAT-CGCTTCGGTGAGATAG-3' (SEQ ID NO: 3) by hybridization to the ligation template oligonucleotide of sequence 5'-CTCATCCTGCGAACCA-CTATCT-CACCGAAGCG-3' (SEQ ID NO: 4), which acts as a circularization splint. The circularized oligonucleotide also contains the randomly generated UMI barcode "Nx22" as well as PPBS1 and the Forward PCR primer site (F-PCR"). The ligation template oligonucleotide for type 1 RCA products can also be used to prime the RCA reaction.

After amplification, the type 1 RCA product is a concatemer of the following sequence: 5'CTATCTCACCGAAGCG ATAAATCCTCCGTCTACCTTCA NNNNNNNNNNNNNNNNNNNNNN GTATTTGAGT-TAGACTCCCGGC CTCATCCTGCGAACCA-3' (SEQ ID NO: 5).

In this example, a primer that binds to F-PCR (of sequence GCCGGGAGTCTAACTCAAATAC; SEQ ID NO: 6) in the type 1 RCA product is extended during a bulk manufacturing step, thereby copying the UMI in a gap-fill polymerization/ligation reaction onto the 5'-end of the PPBS 1-oligo (5' P-TGAAGGTAGACGGAGGATTTAT-AAAAAAA-GATCATGCAACGTATTGAAACG (SEQ ID NO:20).

Type 2 RCA Products

The following oligonucleotide is circularized: 5'-P-TAGTGAGTGTACGGAC CAACATCAGTAT-TCCCAGGCTA NNNNNNNNNNNNNNNNNNNNNN GTGCTGACCAATCGACCAAGAT CGCCTAGTCTC-TACTA-3'(SEQ ID NO: 7) by hybridization to the ligation template oligonucleotide of sequence 5-GTCCGTACACT-CACTATAGTAGAGACTAGGCG-3 (SEQ ID NO: 8), which acts as a circularization splint. The circularized oligonucleotide also contains the randomly generated UMI barcode "Nx22" as well as PPBS2 and the Reverse PCR primer site ("R-PCR"). The ligation template oligonucleotide for type 2 RCA products can also be used to prime the RCA reaction.

After amplification, the type 2 RCA product is a concatemer of the following sequence: 5'-TAGTAGA-GACTAGGCG-ATCTTGGTCGATTGGTCAGCAC-NNNNNNNNNNNNNNNNNNNNNN-TAGCCTGGGAATACTGATGTTG-GTCCGTACACTCACTA-3' (SEQ ID NO: 9).

In this example, during bulk production of RCA products, the 3' end of the PPBS2-oligo (P-CTA-GACGCTGTAGTTCTGTAGC-AAAAAAA-CAA-CATCAGTATTCCCAGGCTA-3' (SEQ ID NO:16) hybridizes to its binding site in the type 2 RCA product and is extended, thereby copying the UMI in a gap-fill polymerization/ligation reaction. The 3' end of the PPBS2-oligo is extended until it meets the 5' end of an oligonucleotide of sequence 5'-P-GTGCTGACCAATCGACCAAGAT (SEQ ID NO: 10). The 3' end of this extension product ligates to the 5'-P end of the oligonucleotide.

These steps result in a bulk production of RCA-products of two types, both carrying multiple 3'-free or 5'-free oligonucleotides capable of reacting and ready for use in the sample assay as seen in FIG. 13.

Ligation Reaction on Sample Forming the Complete Grid-Oligo

As shown in FIG. 14, the Grid-oligo is formed by uniting three oligonucleotides by splinted ligation reactions. The target binding probe(s) is allowed to bind the sample. Ligation splint oligonucleotides (PPBS1+probe splint 5' GCTATTCAATTGTCTCCTATGT-CGTTT-CAATACGTTGCATGATC (SEQ ID NO:17), and PPBS2+probe splint GCTACAGAACTA-CAGCGTCTAG-TGTCTGAGCGCGCGTAATTCAT (SEQ ID NO:18) are added to the target binding probes to enable their ligation to the PPBS1 and PPBS2 oligos. These splints can preferably contain Uracil substitutes for Thymidine to enable enzymatic Uracil-N-glycosylase degradation post-ligation in order to reduce likelyhood of false PCR-jumping.

After the target probes containing the splints have bound the sample the RCA-products type 1 and type 2 are added as functionalized above. The free ends of PPBS1 and PPBS2 will respectively bind to each end of the Grid oligo middle section (part 1) via the splints. A DNA ligation enzyme is added to covalently unite p-UMI from RCA-product type-1 with TP-BC and P-UMI on RCA-product type-2.

PCR Amplification

The ligation reaction has united the grid oligonucleotide components (and hence the TP-BC sequence) with the complements of two UMIs, one from a type 1 RCA product and the other from a type 1 RCA product. This product is amplified by PCR using the following primers: F-PCR primer 5'GTATTTGAGTTAGACTCCCGGC-3' (SEQ ID NO: 11) and R-PCR primer 5'ATCTTGGTCGAT-TGGTCAGCAC-3' (SEQ ID NO: 12).

The PCR product produced in this rejection will have the following sequences containing these elements: F-primer, Pixel-1 UMI, PPBS1, pA-linker, Ligation sequence, pA-linker, TP-BC, pA-linker, Ligation sequence, pA-linker, PPBS2, Pixel-2 UMI, R-primer. In this example, the product will have the sequence GCCGGGAGTCTAACT-CAAATAC-Nx22-TGAAGGTAGACGGAGGATTTAT-AAAAAAA-GATCATGCAACGTATTGAAACG-ACAT-AGGAGACAATTGAATAGC-AAAAAAA-TGGCACCGGACCGTCTGAAATG-AAAAAAA-ATGAATTACGCGCGCTCAGACA-CTAGACGCTGTAGTTCTGTAGC-AAAAAAA-CAACATCAGTATTCCCAGGCTA-Nx22-GTGCTGACCAATCGACCAAGAT (SEQ ID NO: 19). The PCR amplification may contain additional Primer sequences useful for labeling each sample uniquely to enable downstream pooling of multiple samples prior to sequencing, so called sample barcoding.

Example 13

Figure 15:
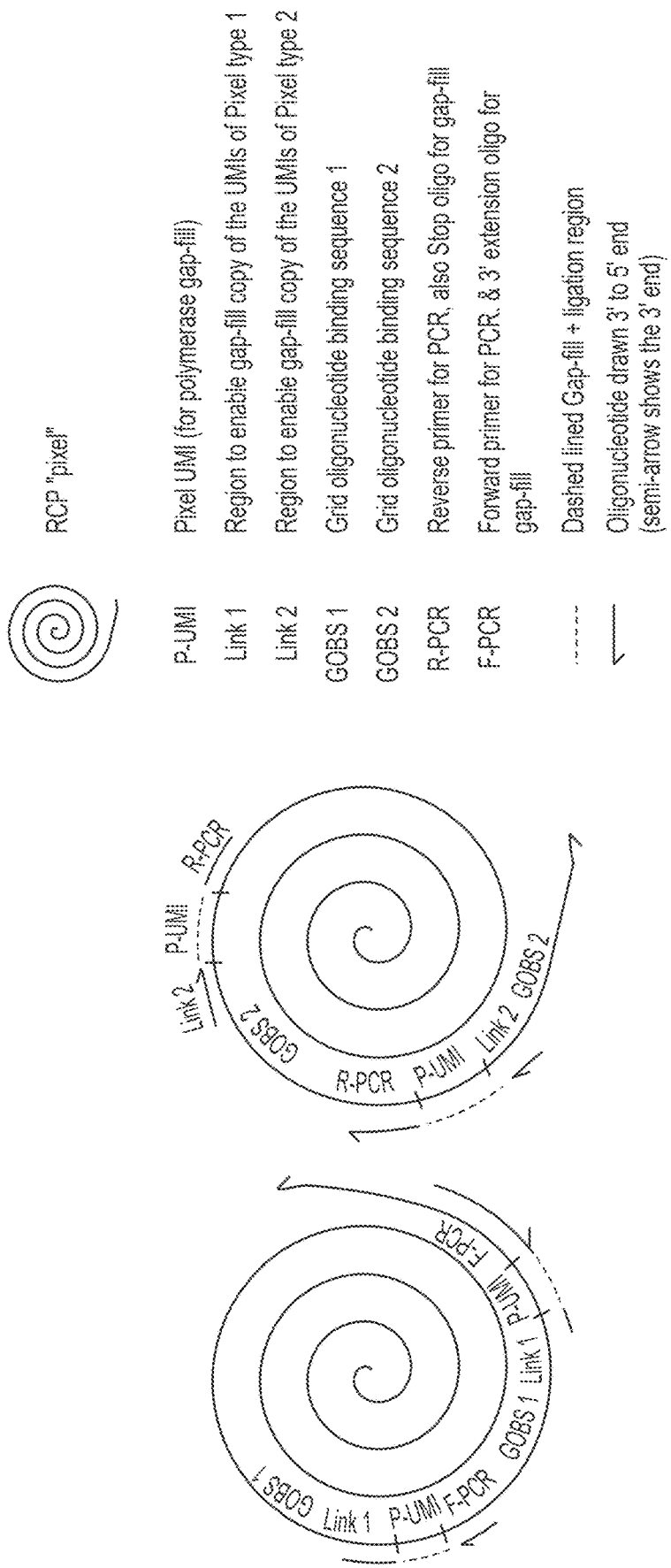
FIG. 15 schematically illustrates the first part of an eighth implementation of the present method.
Figure 16:
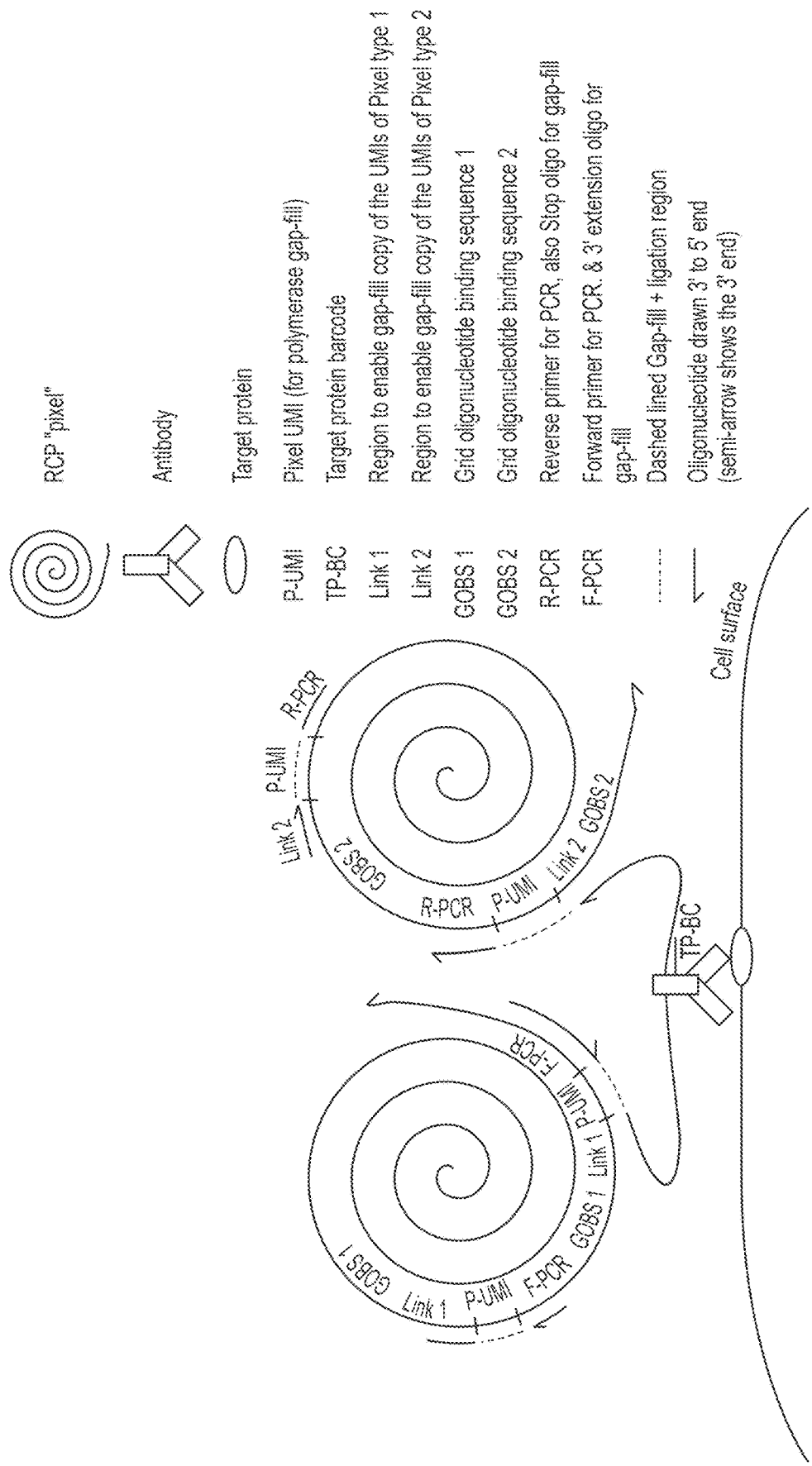
FIG. 16 schematically illustrates the second part of the eighth implementation of the present method.

An eight implementation of the method is shown in FIGS. 15 and 16. FIG. 15 shows how the RCA products are designed, which is similar to the method shown in FIG. 10. This version used a pre-preparation step of the two types of RCP-pixels used in order to enable a DNA ligation-based sensing of samples. Pixels are first made partially double-stranded by gap-fill polymerization across the UMIs. Two types of pixels are made having either a GOBS-1 or -2 site capable of hybridizing to the grid oligonucleotide in the assay step shown in in FIG. 16. FIG. 16 shows the sample is bound by the target analyte sensing probes which carry the grid-oligonucleotides. The RCA products are then added to the sample and the GOBS1 and GOBS2 are allowed to hybridize to the grid oligo-ends forming a nick, sealable by a DNA ligation reaction forming the PCR amplicon. The product can be sequenced to determine the UMIs of the RCA products.

The invention claimed is:

1. A method comprising:
   (a) producing rolling circle amplification (RCA) products that are immobilized in or on cells, wherein each RCA product has an RCA product identifier sequence that distinguishes the RCA product from other RCA products that are immobilized in or on the cells;
   (b) while the RCA products are immobilized in or on the cells, producing nucleic acid products that contain RCA product identifier sequences and/or complements thereof from adjacent RCA products;
   (c) for each of a plurality of the nucleic acid products of (b), identifying which RCA product identifier sequences and/or complements thereof are in the nucleic acid product; and
   (d) making a physical map of at least some of the RCA products of (a) using the RCA product identifier sequences and/or complements thereof identified in (c).

2. The method of claim 1, wherein (c) is done by sequencing the nucleic acid products produced in (b) to obtain sequence reads, and analyzing the sequence reads.

3. The method of claim 1, wherein (c) comprises identifying which RCA product identifier sequences are united in the nucleic acid products of (b).

4. The method of claim 1, wherein (b) is done by ligation, gap-fill ligation, primer extension, or any combination thereof.

5. The method of claim 1, wherein the RCA products are immobilized in or on the cells via an antibody.

6. The method of claim 5, wherein each RCA product further comprise a barcode sequence that identifies the antibody to which it is bound and step (d) comprises making the physical map of at least some of the RCA products and identifying the antibodies to which they are bound.

7. The method of claim 1, wherein the cells are blood cells, or a sub-population thereof.

8. The method of claim 1, wherein the cells are disassociated cells or a cell suspension.

9. The method of claim 1, wherein the cells are in a tissue section or a three-dimensional sample of tissue.

10. The method of claim 1, wherein the cells are mammalian cells.

11. The method of claim 1, wherein step (b) is done by extending both ends of a grid oligonucleotide that is hybridized to the adjacent RCA products, thereby copying the complements of the RCA product identifier sequences from the adjacent RA products onto the ends of the grid oligonucleotide.

12. The method of claim 11, wherein the RCA products of (a) comprise a first type of RCA product and a second type of RCA product, and wherein the 5' end of the grid oligonucleotide hybridizes to the first type of RCA product but not the second type of RCA product, and wherein the 3' end of the grid oligonucleotide hybridizes to the second type of RCA product but not the first type of RCA product.

13. The method of claim 1, wherein the RCA products are made by performing a rolling circle amplification reaction in situ in or on the cells.

* * * * *

SEQUENCE LISTING

```
Sequence total quantity: 20
SEQ ID NO: 1          moltype = DNA  length = 27
FEATURE               Location/Qualifiers
misc_feature          1..27
                      note = synthetic sequence
source                1..27
                      mol_type = other DNA
                      organism = synthetic construct
```

```
SEQUENCE: 1
tcgggatcgg catcgacgcc taaaaaa                                         27

SEQ ID NO: 2            moltype = DNA   length = 80
FEATURE                 Location/Qualifiers
misc_feature            1..80
                        note = synthetic sequence
misc_feature            51^52
                        note = TP-BC is present between the nucleotides.
source                  1..80
                        mol_type = other DNA
                        organism = synthetic construct
SEQUENCE: 2
tgaaggtaga cggaggattt ataaaaaaat aggcgtcgat gccgatcccg aaaaaaaaca     60
acatcagtat tcccaggcta                                                 80

SEQ ID NO: 3            moltype = DNA   length = 98
FEATURE                 Location/Qualifiers
misc_feature            1..98
                        note = synthetic sequence
misc_difference         39..60
                        note = n is a, c, g, or t
source                  1..98
                        mol_type = other DNA
                        organism = synthetic construct
SEQUENCE: 3
tggttcgcag gatgaggccg ggagtctaac tcaaatacnn nnnnnnnnnn nnnnnnnnnn     60
tgaaggtaga cggaggattt atcgcttcgg tgagatag                             98

SEQ ID NO: 4            moltype = DNA   length = 32
FEATURE                 Location/Qualifiers
misc_feature            1..32
                        note = synthetic sequence
source                  1..32
                        mol_type = other DNA
                        organism = synthetic construct
SEQUENCE: 4
ctcatcctgc gaaccactat ctcaccgaag cg                                   32

SEQ ID NO: 5            moltype = DNA   length = 98
FEATURE                 Location/Qualifiers
misc_feature            1..98
                        note = synthetic sequence
misc_difference         39..60
                        note = n is a, c, g, or t
source                  1..98
                        mol_type = other DNA
                        organism = synthetic construct
SEQUENCE: 5
ctatctcacc gaagcgataa atcctccgtc taccttcann nnnnnnnnnn nnnnnnnnnn     60
gtatttgagt tagactcccg gcctcatcct gcgaacca                             98

SEQ ID NO: 6            moltype = DNA   length = 22
FEATURE                 Location/Qualifiers
misc_feature            1..22
                        note = synthetic sequence
source                  1..22
                        mol_type = other DNA
                        organism = synthetic construct
SEQUENCE: 6
gccgggagtc taactcaaat ac                                              22

SEQ ID NO: 7            moltype = DNA   length = 98
FEATURE                 Location/Qualifiers
misc_feature            1..98
                        note = synthetic sequence
misc_difference         39..60
                        note = n is a, c, g, or t
source                  1..98
                        mol_type = other DNA
                        organism = synthetic construct
SEQUENCE: 7
tagtgagtgt acggaccaac atcagtattc ccaggctann nnnnnnnnnn nnnnnnnnnn     60
gtgctgacca atcgaccaag atcgcctagt ctctacta                             98

SEQ ID NO: 8            moltype = DNA   length = 32
FEATURE                 Location/Qualifiers
misc_feature            1..32
                        note = synthetic sequence
```

```
source              1..32
                    mol_type = other DNA
                    organism = synthetic construct
SEQUENCE: 8
gtccgtacac tcactatagt agagactagg cg                                        32

SEQ ID NO: 9        moltype = DNA   length = 98
FEATURE             Location/Qualifiers
misc_feature        1..98
                    note = synthetic sequence
misc_difference     39..60
                    note = n is a, c, g, or t
source              1..98
                    mol_type = other DNA
                    organism = synthetic construct
SEQUENCE: 9
tagtagagac taggcgatct tggtcgattg gtcagcacnn nnnnnnnnnn nnnnnnnnnn          60
tagcctggga atactgatgt tggtccgtac actcacta                                  98

SEQ ID NO: 10       moltype = DNA   length = 22
FEATURE             Location/Qualifiers
misc_feature        1..22
                    note = synthetic sequence
source              1..22
                    mol_type = other DNA
                    organism = synthetic construct
SEQUENCE: 10
gtgctgacca atcgaccaag at                                                   22

SEQ ID NO: 11       moltype = DNA   length = 22
FEATURE             Location/Qualifiers
misc_feature        1..22
                    note = synthetic sequence
source              1..22
                    mol_type = other DNA
                    organism = synthetic construct
SEQUENCE: 11
gtatttgagt tagactcccg gc                                                   22

SEQ ID NO: 12       moltype = DNA   length = 22
FEATURE             Location/Qualifiers
misc_feature        1..22
                    note = synthetic sequence
source              1..22
                    mol_type = other DNA
                    organism = synthetic construct
SEQUENCE: 12
atcttggtcg attggtcagc ac                                                   22

SEQ ID NO: 13       moltype = DNA   length = 124
FEATURE             Location/Qualifiers
misc_feature        1..124
                    note = synthetic sequence
misc_feature        22^23
                    note = A randomly generated UMI barcode "Nx22" is present
                     between the nucleotides
misc_feature        102^103
                    note = A randomly generated UMI barcode "Nx22" is present
                     between the nucleotides
source              1..124
                    mol_type = other DNA
                    organism = synthetic construct
SEQUENCE: 13
gccgggagtc taactcaaat actgaaggta gacggaggat ttataaaaaa ataggcgtcg          60
atgccgatcc cgaaaaaaaa caacatcagt attcccaggc tagtgctgac caatcgacca         120
agat                                                                      124

SEQ ID NO: 14       moltype = DNA   length = 27
FEATURE             Location/Qualifiers
misc_feature        1..27
                    note = synthetic sequence
source              1..27
                    mol_type = other DNA
                    organism = synthetic construct
SEQUENCE: 14
catttcagac ggtccggtgc caaaaaa                                              27

SEQ ID NO: 15       moltype = DNA   length = 80
FEATURE             Location/Qualifiers
```

```
misc_feature       1..80
                   note = synthetic sequence
source             1..80
                   mol_type = other DNA
                   organism = synthetic construct
SEQUENCE: 15
acataggaga caattgaata gcaaaaaaat ggcaccggac cgtctgaaat gaaaaaaaat    60
gaattacgcg cgctcagaca                                                80

SEQ ID NO: 16      moltype = DNA  length = 51
FEATURE            Location/Qualifiers
misc_feature       1..51
                   note = synthetic sequence
source             1..51
                   mol_type = other DNA
                   organism = synthetic construct
SEQUENCE: 16
ctagacgctg tagttctgta gcaaaaaaac aacatcagta ttcccaggct a              51

SEQ ID NO: 17      moltype = DNA  length = 44
FEATURE            Location/Qualifiers
misc_feature       1..44
                   note = synthetic sequence
source             1..44
                   mol_type = other DNA
                   organism = synthetic construct
SEQUENCE: 17
gctattcaat tgtctcctat gtcgtttcaa tacgttgcat gatc                     44

SEQ ID NO: 18      moltype = DNA  length = 44
FEATURE            Location/Qualifiers
misc_feature       1..44
                   note = synthetic sequence
source             1..44
                   mol_type = other DNA
                   organism = synthetic construct
SEQUENCE: 18
gctacagaac tacagcgtct agtgtctgag cgcgcgtaat tcat                     44

SEQ ID NO: 19      moltype = DNA  length = 228
FEATURE            Location/Qualifiers
misc_feature       1..228
                   note = synthetic sequence
misc_feature       22^23
                   note = A randomly generated UMI barcode "Nx22" is present
                    between the nucleotides
misc_feature       205^206
                   note = A randomly generated UMI barcode "Nx22" is present
                    between the nucleotides
source             1..228
                   mol_type = other DNA
                   organism = synthetic construct
SEQUENCE: 19
gccgggagtc taactcaaat acntgaaggt agacggagga tttataaaaa aagatcatgc    60
aacgtattga aacgacatag gagacaattg aatagcaaaa aaatggcacc ggaccgtctg   120
aaatgaaaaa aaatgaatta cgcgcgctca gacactagac gctgtagttc tgtagcaaaa   180
aaacaacatc agtattccca ggctangtgc tgaccaatcg accaagat                228

SEQ ID NO: 20      moltype = DNA  length = 51
FEATURE            Location/Qualifiers
misc_feature       1..51
                   note = synthetic sequence
source             1..51
                   mol_type = other DNA
                   organism = synthetic construct
SEQUENCE: 20
tgaaggtaga cggaggattt ataaaaaaag atcatgcaac gtattgaaac g              51
```